(12) United States Patent
Blömker et al.

(10) Patent No.: US 9,079,828 B2
(45) Date of Patent: Jul. 14, 2015

(54) POLYMERIZABLE COMPOUNDS COMPRISING A POLYALICYLIC STRUCTURE ELEMENT

(75) Inventors: Tobias Blömker, Cuxhaven (DE); Manfred Stepputtis, Kutenholz (DE); Manfred Thomas Plaumann, Cuxhaven (DE); Reinhard Maletz, Cuxhaven (DE); Nils Fontein, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 747 days.

(21) Appl. No.: 13/248,920

(22) Filed: Sep. 29, 2011

(65) Prior Publication Data
US 2012/0082959 A1  Apr. 5, 2012

(30) Foreign Application Priority Data

Sep. 30, 2010  (DE) ........................ 10 2010 041 792
Sep. 29, 2011  (EP) ..................................... 11183333

(51) Int. Cl.
| | |
|---|---|
| *C07C 275/60* | (2006.01) |
| *C07C 275/62* | (2006.01) |
| *A61K 6/00* | (2006.01) |
| *A61K 6/083* | (2006.01) |

(52) U.S. Cl.
CPC ............ *C07C 275/60* (2013.01); *A61K 6/0038* (2013.01); *A61K 6/083* (2013.01); *C07C 275/62* (2013.01); *C07C 2103/68* (2013.01); *C07C 2103/74* (2013.01)

(58) Field of Classification Search
CPC  C07C 275/60; C07C 275/62; C07C 2103/68; C07C 2103/74
USPC .................................................. 560/158, 220
See application file for complete search history.

(56) References Cited

U.S. PATENT DOCUMENTS

| | | | |
|---|---|---|---|
| 3,517,039 A | 6/1970 | Wagner et al. | |
| 4,160,080 A | 7/1979 | Koenig et al. | |
| 4,323,696 A | 4/1982 | Schmitz-Josten et al. | |
| 4,447,520 A | 5/1984 | Henne et al. | |
| 4,744,827 A * | 5/1988 | Winkel et al. ................... | 106/35 |
| 4,769,485 A | 9/1988 | Urano et al. | |
| 4,772,530 A | 9/1988 | Gottschalk et al. | |
| 4,874,450 A | 10/1989 | Gottschalk | |
| 4,925,982 A | 5/1990 | Urano et al. | |
| 4,954,414 A | 9/1990 | Adair et al. | |
| 5,055,372 A | 10/1991 | Shanklin et al. | |
| 5,055,544 A * | 10/1991 | Harris et al. .................... | 528/59 |
| 5,057,393 A | 10/1991 | Shanklin et al. | |
| 5,063,257 A | 11/1991 | Akahane et al. | |
| 5,580,947 A | 12/1996 | Brahm et al. | |
| 6,670,499 B1 | 12/2003 | Unoue et al. | |
| 7,081,485 B2 | 7/2006 | Suh et al. | |
| 7,144,927 B1 | 12/2006 | Engelbrecht et al. | |
| 7,148,382 B2 | 12/2006 | Wolf et al. | |
| 7,381,785 B2 | 6/2008 | Detrembleur et al. | |
| 2004/0266906 A1 | 12/2004 | Klee et al. | |
| 2007/0027229 A1 | 2/2007 | Moszner et al. | |

FOREIGN PATENT DOCUMENTS

| | | |
|---|---|---|
| DE | 3338077 A1 | 5/1985 |
| DE | 3703120 A1 | 1/1988 |
| DE | 4231579 A1 | 3/1993 |
| DE | 4416857 A1 | 6/1995 |
| DE | 19903177 A1 | 7/2000 |
| DE | 10119831 A1 | 10/2002 |
| DE | 10352260 B3 | 4/2005 |
| DE | 102004060285 A1 | 6/2006 |
| DE | 60116142 T2 | 7/2006 |
| DE | 102006019092 A1 | 3/2007 |
| DE | 102006050153 A1 | 5/2008 |
| DE | 102007040240 A1 | 2/2009 |
| DE | 102007040239 A1 | 5/2009 |
| EP | 0057474 A2 | 7/1979 |
| EP | 0007508 A2 | 2/1980 |
| EP | 0047902 A2 | 8/1981 |
| EP | 0049631 A1 | 10/1981 |
| EP | 0059451 A1 | 2/1982 |
| EP | 0106176 A1 | 4/1984 |
| EP | 0173567 A2 | 8/1985 |
| EP | 0184095 B1 | 11/1985 |
| EP | 0206074 A2 | 6/1986 |
| EP | 0209700 A2 | 6/1986 |
| EP | 0262629 B1 | 3/1988 |
| EP | 0325266 A2 | 7/1989 |
| EP | 0366977 B1 | 10/1989 |
| EP | 0611752 A1 | 8/1994 |
| EP | 0682012 A1 | 4/1995 |
| EP | 0712840 B1 | 5/1996 |
| EP | 0783880 A2 | 7/1997 |
| EP | 0948955 B1 | 6/1998 |
| EP | 0867457 B1 | 9/1998 |
| EP | 0980682 B1 | 8/1999 |
| EP | 1112995 B1 | 9/1999 |
| EP | 1563821 A1 | 1/2001 |
| EP | 1236459 B1 | 7/2001 |
| EP | 1238993 A1 | 9/2002 |
| EP | 1645582 A1 | 4/2006 |
| EP | 1839640 A2 | 3/2007 |
| GB | 1110673 | 4/1968 |

(Continued)

*Primary Examiner* — Paul A Zucker
*Assistant Examiner* — Mark Luderer
(74) *Attorney, Agent, or Firm* — Duane Morris LLP; J. Rodman Steele, Jr.; Gregory M. Lefkowitz

(57) ABSTRACT

Novel polymerizable compounds comprising a polyalicyclic structure element and certain functional groups, mixtures comprising one or a plurality of these compounds and corresponding curable blends and products as well as their respective use as dental material or for the preparation of a dental material are described. A method for preparing these compounds or mixtures and a method for preparing a product, preferably a product suitable for dentistry, are also described.

16 Claims, No Drawings

(56) References Cited

FOREIGN PATENT DOCUMENTS

| | | |
|---|---|---|
| GB | 2310855 A | 9/1997 |
| JP | 7206740 | 8/1995 |
| WO | 02092021 A1 | 11/2002 |
| WO | 02092023 A1 | 11/2002 |
| WO | 2005084611 A1 | 9/2005 |
| WO | 2006063891 A1 | 6/2006 |
| WO | 2009065873 A2 | 5/2009 |

* cited by examiner

POLYMERIZABLE COMPOUNDS COMPRISING A POLYALICYLIC STRUCTURE ELEMENT

CROSS-REFERENCE TO RELATED APPLICATIONS

This application claims priority to German Application No. DE 10 2010 041 792.0-43 filed Sep. 30, 2010, and European Application No. EP 11 183 333, filed Sep. 29, 2011, the entireties of which are incorporated herein by reference.

FIELD OF THE INVENTION

The present invention relates to novel polymerizable compounds (hereinafter referred to as monomers) comprising a polyalicyclic structure element and certain functional groups, mixtures comprising one or a plurality of these compounds and corresponding curable blends and products as well as their respective use as dental material or for the preparation of a dental material. The invention further relates to a method for preparing these compounds or mixtures and a method for preparing a product, preferably a product suitable for dentistry.

BACKGROUND OF THE INVENTION

Curable monomers comprising a polyalicyclic structure element are substantially known and are used in numerous applications, such as dental engineering.

Within the context of the present text (meth)acrylic means both acrylic and methacrylic.

EP 1 238 993 describes a method for producing polyisocyanates containing acyl urea groups and mixtures of these and their use as starting components for the preparation of polyurethane synthetic materials.

DE 43 14 252 A1 (corresponding to U.S. Pat. No. 5,580, 947) relates to a method for preparation of olefinically unsaturated isocyanates through reaction of isophorone diisocyanate and selected olefinically unsaturated carboxylic acids. The resultant olefinically unsaturated isocyanates are suitable for use as binding agents in coating materials.

U.S. Pat. No. 3,517,039 describes acylated urea polyisocyanates, prepared by reacting organic diisocyanates with organic monocarboxylic acids. The products described in U.S. Pat. No. 3,517,039 can be used for the preparation of heat-resistant foams or polyurethane elastomers as well as in particular elastified lacquer coatings.

EP 0 611 752 A1 discloses a method for preparation of olefinically unsaturated isocyanates comprising urethane groups while maintaining a certain NCO/OH equivalent ratio. The isocyanates that can be obtained according to EP 0 611 752 A1 can be used as binding agents for coating materials to be used at room temperature in single component form.

EP 0 209 700 A2, DE 35 22 006 and DE 35 22 005 describe (meth)acrylic acid derivatives of certain tricyclodecenes with divalent bridge members from the group of urethanes or ureas, which can be used in the area of dentistry.

EP 0 000 194 A1 (corresponding to U.S. Pat. No. 4,160, 080) describes polyisocyanates, containing allophanate groups. These allophanate polyisocyanates may be used for the preparation of polyurethane foams, elastomers, duromers, coatings, adhesives and lacquers.

EP 0 682 012 B1 relates to a method for the preparation of bright-colored, light stable (cyclo-aliphatic) polyisocyanates comprising allophanate groups, by reacting organic compounds having urethane groups with organic polyisocyanates with (cyclo)aliphatically bonded isocyanate groups in the presence of tin(II) salts. The polyisocyanates described in EP 0 682 012 B1 can be used as synthesis components in the preparation of polyurethane synthetic materials.

EP 1 727 846 B1 discloses a method for preparation of binding agents containing allophanate groups, comprising groups reacting with ethylenically unsaturated compounds under polymerization under the effects of actinic radiation.

EP 0 712 840 B1 relates to a method for producing certain polyisocyanates comprising allophanate groups through the reaction of compounds comprising urethane groups with the formation of allophanate. The compounds according to EP 0 712 840 B1 can be used as binding agents or binding agent components in coating media.

EP 0 867 457 B1 discloses an ethylenically unsaturated polyurethane, which is substantially free from isocyanate groups, which is the reaction product of an ethylenically unsaturated polyisocyanate, containing allophanate groups and β,γ-ethylenically unsaturated ether groups, with a hydroxyfunctional, ethylenically unsaturated compound, wherein the ethylenically unsaturated polyisocyanate is prepared by allophantization of the urethane groups-containing reaction products of an organic diisocyanate with a β,γ-ethylenically unsaturated ether alcohol, wherein the β,γ-ethylenically unsaturated ether alcohol is selected from the group consisting of glycerin diallyl ether, trimethylolpropane diallyl ether and pentaerythritriallyl ether. The ethylenically unsaturated polyurethanes with allophanate groups disclosed in EP 0 867 457 B1 can be used as binding agents in single component coating compositions.

DE 10 2007 040 240 A1 and EP 1 645 582 A1 in each case describe a method for preparation of radiation-curing allophanates through the reaction of compounds containing isocyanate groups and hydroxyfunctional compounds, wherein the ratio of NCO groups to OH groups is 1.45:1.0 through 1.1:1.0. According to DE 10 2007 040 239 A1 with the use of certain mixtures containing hydroxyethylacrylate and hydroxypropylacrylate as the hydroxyfunctional compounds corresponding radiation-curing allophanates are obtained. The radiation-curing allophanates according to these three documents can be used for the preparation of coatings and lacquers, as well as adhesives, inks, casting resins, dental compounds, release agents, photoresists, stereolithography systems, resins for composites and sealants.

DE 10 2004 060 285 A1 relates to radiation-curable compounds based on a dicidol mixture (containing two or three isomers 3,8-, 4,8- and/or 5,8-bis(hydroxymethyl)tricyclo[5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 10 2004 060 285 A1 can be used as radiation-induced-curing coating materials, adhesives, laminations, printing and other inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE 10 2004 060 285 A1.

WO 03/035013 A1 and DE 602 16 951 T2 relate to dental adhesive compositions for bonding dental restoratives to dentin and/or enamel. In these documents, the preparation of 3,(4),8,(9)-Bis(2-propenamidomethyl)tricyclo[5.2.1.0]$^{2,6}$-decan, amongst others, is described.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

In the area of dental engineering and for various other application there is a constant need for further polymerizable monomers. There is in particular a need for monomers which allows the preparation of products and polymers with improved characteristics, for example an increased hydrophobia and/or a higher mechanical stability.

DESCRIPTION OF THE INVENTION

The primary object for the invention is to provide novel polymerizable monomers which are in particular suitable for applications in dental engineering, although without being limited to this area of use. Preferably, the polymers obtainable through the use of the monomers according to the invention should have a pronounced hydrophobia which inter alia manifests itself in very low water absorption. Similarly preferably, the polymers obtainable through the use of monomers according to the invention should be characterized by high mechanical stability which inter alia manifests itself in a high flexural strength. Particularly preferably, through the use of monomers according to the invention it should be possible to prepare polymers that have both a low water absorption and a high flexural strength.

These objects are achieved by a compound of structure $Q(YZ_e)_b$ with one, two, three, four or a plurality of functional groups selected from the group consisting of N-acyl urea, allophanate and biuret, wherein here and below the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups;

b is an integer selected from the group of integers 2, 3, 4;

each Z represents a structure element, which independently of any further structure elements Z is selected from the group consisting of

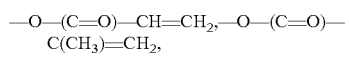

—O—(C=O)—CH=CH$_2$, —O—(C=O)—C(CH$_3$)=CH$_2$,

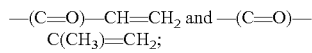

—(C=O)—CH=CH$_2$ and —(C=O)—C(CH$_3$)=CH$_2$;

each index e is an integer, which independently of any further indices e is selected from the group of integers 1, 2, 3 and 4;

each Y represents a structure element, which in the structure $Q(YZ_e)_b$ bonds the polyalicyclic structure element Q with e structure elements Z;

wherein the compound is preparable by conversion of a first reaction product, which is the reaction product of a first reaction of A) a compound of structure $QG_b$, in which each G represents a reactive group, which independently of further groups G is selected from the group consisting of (—CH$_2$)$_n$—NH$_2$, (—CH$_2$)$_n$—(OCH$_2$—CHR)$_m$—OH, (—CH$_2$)$_n$—NCO and (—CH$_2$)$_n$—COOH with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COOH, wherein the following applies:

R in each case independently of any further R represents a hydrogen atom or an alkyl radical;

m is an integer selected from the group of integers from 0 through 10, each index n is an integer, which independently of any other indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

In the area of dental engineering dental polymers are subject to particular requirements, such as for example good biocompatibility, low toxicity of the monomer (in the event that it does not polymerize, but remains in part as a monomer in the polymer matrix), a lower residual monomer content, etc.

The polymers obtainable through the use of the monomers according to the invention have a pronounced hydrophobia which inter alia manifests itself in very low water absorption of the polymers. The polymers obtainable through the use of the monomers according to the invention are also characterized by a high mechanical stability which inter alia manifests itself in a high flexural strength of the polymers. The monomers according to the invention, in particular according to the particularly preferred configurations and embodiments, lend themselves to the preparation of polymers which have both a low water absorption and a high flexural strength. The polyalicyclic structure element Q, in particular in the preferred and particularly preferred configurations, contributes toward the high level of hydrophobia which inter alia manifests itself in very low water absorption by the polymers.

It has been found that the monomers according to the invention are easy to process. The monomers according to the invention are homo- or copolymerizable, wherein the cured polymers or molding materials have low shrinkage, good adhesion to various substrates, a high resistance to hydrolysis, a low water absorption, a high mechanical strength and a high sheen. The stated characteristics are in particular important in the area of dental engineering.

In particular the preferred and particularly preferred compounds according to the invention allow a high degree of crosslinking and are also preferably radically cross-linkable. Due to their highly functionalized structure they have a high probability of cross-linking and polymerization.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

A monomer according to the invention comprises at least one polyalicyclic structure element Q, derived from a corresponding polyalicyclic hydrocarbon. In the context of the present text, this means that b hydrogen atoms of the hydrocarbon are replaced by substituents $YZ_e$ (as described above), and optionally one, two or a plurality of the hydrogen atoms not substituted by substituents $YZ_e$ are substituted by alkyl groups, alkoxy groups, halogen atoms or trifluoromethyl groups. The polyalicyclic structure element Q is constituted by carbon ring atoms. Carbon atoms outside the rings are a component of substituents.

The structure of unsubstituted bicycles is as follows:

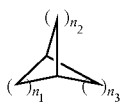

wherein $n_1$, $n_2$ and $n_3$ in each case independently or one another can represent an integer from 1 through 8, preferably an integer from 1 through 4.

The following examples are provided:

| | |
|---|---|
| For $n_1 = n_2 = 1$; $n_3 = 2$ | bicyclo[2.1.1]hexane |
| for $n_1 = 1$; $n_2 = n_3 = 2$ | bicyclo[2.2.1]heptane |
| for $n_1 = n_2 = 1$; $n_3 = 3$ | bicyclo[3.1.1]heptane |
| for $n_1 = n_2 = n_3 = 2$ | bicyclo[2.2.2]octane |
| for $n_1 = n_2 = 1$; $n_3 = 4$ | bicyclo[4.1.1]octane |
| for $n_1 = 1$; $n_2 = 2$; $n_3 = 3$ | bicyclo[3.2.1]octane |
| for $n_1 = 1$; $n_2 = 2$; $n_3 = 4$ | bicyclo[4.2.1]nonane |
| for $n_1 = n_2 = 2$; $n_3 = 4$ | bicyclo[4.2.2]decane |

A number of examples of disubstituted bicycles are shown below:

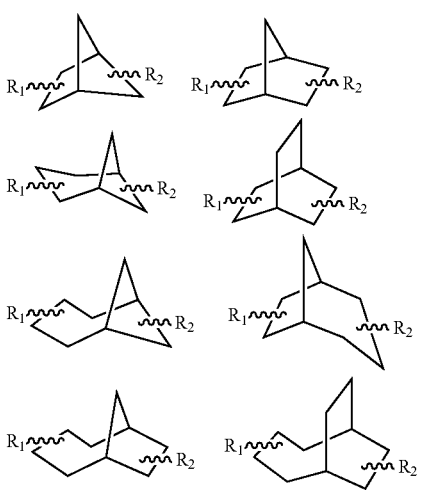

wherein R1 and R2 in each case represent the other radicals of the compound.

Examples of bicyclic structure elements Q are the bicyclo[1.1.1]pentane, bicyclo[2.1.1]hexane, bicyclo[2.2.1]heptane, bicyclo[3.1.1]heptane, bicyclo[2.2.2]octane, bicyclo[4.1.1]octane, bicyclo[3.2.1]octane, bicyclo[4.2.1]nonane, bicyclo[3.3.1]nonane, bicyclo[5.1.1]nonane, bicyclo[3.2.2]nonane, bicyclo[6.1.1]decane, bicyclo[5.2.1]decane, bicyclo[4.2.2]decane, bicyclo[3.3.2]decane, bicyclo[7.1.1]undecane, bicyclo[6.2.1]undecane, bicyclo[5.2.2]undecane, bicyclo[4.3.2]undecane, bicyclo[3.3.3]undecane, bicyclo[8.1.1]dodecane, bicyclo[7.2.1]dodecane, bicyclo[6.2.2]dodecane, bicyclo[5.3.2]dodecane, bicyclo[4.3.3]dodecane, bicyclo[4.4.2]dodecane, bicyclo[5.4.1]dodecane structure elements and even higher structure elements such as the corresponding tridecanes, tetradecanes, pentadecanes, etc.

For unsubstituted tricycles the following structures are possible:

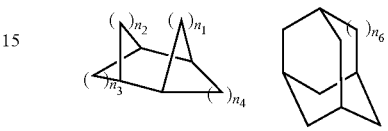

wherein $n_1$, $n_2$, $n_3$, $n_4$ or $n_6$ in each case independently of one another can represent an integer from 0 through 5.

The following examples are provided:

| | |
|---|---|
| For $n_1 = 2$; $n_2 = 0$; $n_3 = 2$; $n_4 = 3$ | tricyclo[4.3.2.0$^{2,5}$]undecane |
| for $n_1 = 0$; $n_2 = 1$; $n_3 = 2$; $n_4 = 3$ | tricyclo[5.2.1.0$^{2,6}$]decane |
| for $n_1 = 0$; $n_2 = 2$; $n_3 = 2$; $n_4 = 3$ | tricyclo[5.2.2.0$^{2,6}$]undecane |
| for $n_1 = 2$; $n_2 = 0$; $n_3 = 2$; $n_4 = 2$ | tricyclo[4.2.2.0$^{2,5}$]decane |
| for $n_6 = 1$ | tricyclo[3.3.1.1$^{3,7}$]decane |

In the following examples of single-, di- or tri-substituted tricycles are shown:

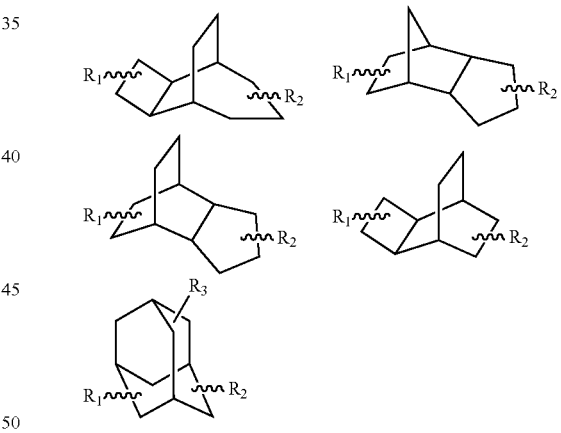

wherein R1, R2 and R3 in each case represent the other radicals of the compound.

Examples of tricyclic structure elements Q are the tricyclo[3.2.1.0$^{2,6}$]octane, tricyclo[4.2.1.0$^{2,6}$]nonane, tricyclo[5.2.1.0$^{2,6}$]decane, tricyclo[6.2.1.0$^{2,6}$]undecane, tricyclo[7.2.1.0$^{2,6}$]dodecane, or tricyclo[4.2.1.1$^{2,5}$]decane, tricyclo[4.3.1.1$^{2,5}$]decane, tricyclo[4.4.1.1$^{2,5}$]decane, tricyclo[2.2.1.0$^{2,6}$]heptane, tricyclo[2.2.2.0$^{2,6}$]octane, tricyclo[3.2.2.0$^{2,6}$]nonane, tricyclo[3.3.1.1$^{3,7}$]decane, tricyclo[3.2.1.1$^{3,7}$]nonane, tricyclo[4.2.2.2$^{2,5}$]dodecane, tricyclo[4.3.2.2$^{2,5}$]tridecane, tricyclo[4.4.2.2$^{2,5}$]tetradecane, tricyclo[4.2.1.0$^{3,7}$]nonane, tricyclo[4.4.1.1$^{1,5}$]dodecane, tricyclo[6.2.1.0$^{2,7}$]undecane, tricyclo[5.2.2.0$^{2,6}$]undecan, tricyclo[6.2.2.0$^{2,7}$]dodecane, tricyclo[4.3.2.0$^{2,5}$]undecane, tricyclo[4.2.2.0$^{2,5}$]decane or the tricyclo[5.5.1.0$^{3,11}$]tridecane structure element.

The following is a possible example for unsubstituted tetracycles:

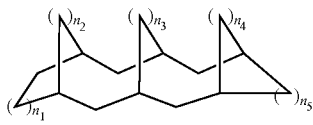

wherein $n_1$, $n_2$, $n_3$, $n_4$, and $n_5$ in each case independently of one another can represent an integer from 1 through 5.

The following examples are provided:

| | |
|---|---|
| For $n_1 = n_2 = n_3 = n_4 = 2$; $n_5 = 5$ | tetracyclo[9.6.2$^{3,9}$.2$^{13,16}$]tricosane |
| for $n_1 = n_5 = 2$; $n_2 = n_3 = n_4 = 1$ | tetracyclo[6.6.1$^{3,6}$.1$^{10,13}$]heptadecane |
| for $n_1 = n_2 = n_3 = n_4 = n_5 = 2$ | tetracyclo[6.6.2$^{3,6}$.2$^{10,13}$]eicosane |

A number of examples of disubstituted tetracycles are shown below:

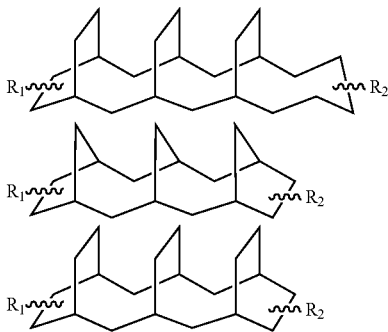

wherein R1 and R2 in each case represent the other radicals of the compound.

Examples of tetracyclic structure elements Q are the tetracyclo[4.4.2.2$^{2,5}$.1$^{7,10}$]pentadecane, tetracyclo[5.5.2.2$^{2,6}$.1$^{8,12}$]heptadecane, tetracyclo[6.6.2.2$^{2,7}$.1$^{9,14}$]nonadecane, tetracyclo[4.4.2.2$^{2,5}$.2$^{7,10}$]hexadecane, tetracyclo[5.4.2.2$^{2,6}$.1$^{8,11}$]hexadecane, tetracyclo[6.2.1.1$^{3,6}$.0$^{2,7}$]dodecan, tetracyclo[9.6.2$^{3,9}$.2$^{13,16}$]tricosan-, tetracyclo[9.6.2$^{3,9}$.2$^{13,16}$]tricosan-, tetracyclo[6.6.1$^{3,6}$.1$^{10,13}$]heptadecane, tetracyclo[6.6.2$^{3,6}$.2$^{10,13}$]cosane, or tetracyclo[5.3.2.1$^{2,4}$.0$^{3,6}$]tridecane structure element.

Examples of pentacyclic structure elements Q are the pentacyclo[4.2.0.0$^{2,5}$.0$^{3,8}$.0$^{4,7}$]octane, pentacyclo[13.7.4.3$^{3,8}$.0$^{18,20}$.1$^{13,28}$]triacontane, pentacyclo[8.6.6.5$^{2,9}$.1$^{23,26}$]octacosane or pentacyclo[3.3.0.0$^{2,4}$.0$^{3,7}$.0$^{6,8}$]octane structure element.

An example of a hexacyclic structure element Q is the hexacyclo[15.3.2.2$^{3,7}$.1$^{2,12}$.0$^{13,21}$.0$^{11,25}$]pentacosane.

Preferred compounds according to A) for preparation of the monomers according to the invention are for example:

Carboxylic acid substituted polyalicyclic hydrocarbons:
bicyclo[3.2.2]nonane-6,7-dicarboxylic acid,
bicyclo[3.3.1]nonane-1,5-dicarboxylic acid,
tricyclo[3.2.2.0$^{2,4}$]non-8-ene-6,7-dicarboxylic acid,
bicyclo(2.2.1)-2,5-heptadiene-2,3-dicarboxylic acid,
bicyclo[2.2.1]heptane-5,6-dicarboxylic acid,
norbornane-2,3-dicarboxylic acid,
bicyclo[2.2.1]hept-5-ene-2,3-dicarboxylic acid,
pentacyclo[4.4.0.0$^{2,5}$.0$^{3,8}$.0$^{4,7}$]decane-2,4-dicarboxylic acid,
bicyclo[2.2.2]octane-1,4-dicarboxylic acid, etc.

Alcohol substituted polyalicyclic hydrocarbons:
bicycle(2.2.1)heptane-2,7-diol,
[5-(hydroxymethyl)-6-bicyclo[2.2.1]hept-2-enyl]-methanol,
tricyclo[3.3.1.1$^{3,7}$]decane-1,3-diethanol,
tetracyclo[6.3.0.0$^{2,6}$.0$^{5,9}$]undecane-3,11-diol,
[6-(Hydroxymethyl)-6-bicyclo[2.2.1]hept-2-enyl]methanol,
tricyclo[3.3.1.1$^{3,7}$]decane-1,3-diol,
bis(hydroxymethyl)tricyclo[5.2.1.0$^{2,6}$]decane, etc.

Isocyanate substituted polyalicyclic hydrocarbons:
bis(2-isocyanatoethyl)-5-norbornene-2,3-dicarboxylate,
2,5 (2,6)-bis(isocyanatomethyl)bicyclo[2.2.1]heptane,
bis(isocyanatoymethyl)tricyclo[5.2.1.0$^{2,6}$]decane, etc.

Mixed or amino-substituted polyalicyclic hydrocarbons:
tricyclo[2.2.1.0$^{2,6}$]heptane-1,3-dicarboxylic acid-3-amino,
tricyclo[3.3.1.1$^{3,7}$]decan-1-ol-3-amino,
pentacyclo[4.3.0.0$^{2,5}$.0$^{3,8}$.0$^{4,7}$]nonane-2,4-diamine,
tricyclo[3.3.1.1$^{3,7}$]decan-1-ol-3-amino,
bis(aminomethyl)tricyclo[5.2.1.0$^{2,6}$]decane, etc.

In a preferred embodiment the structure of the polyalicyclic structure element Q is derived from a bicyclic[a.c.d] hydrocarbon. The letters a, c and d are integers and have the meaning of the IUPAC nomenclature. The total of a, c and d is preferably in the range 3 through 13, preferably in the range 4 through 7.

In a further preferred embodiment the structure of the polyalicyclic structure element is derived from a tricyclic [a.c.d.f]hydrocarbon. The total of a, c, d and f is preferably in the range 6 through 12, preferably in the range 7 through 9.

In a preferred embodiment the structure of the polyalicyclic structure element is derived from a tricyclic[a.2.1.0$^{2,(a+1)}$]hydrocarbon, wherein a can in each case represent 3, 4, 5, 6 or 7.

In a further preferred embodiment the structure of the polyalicyclic structure element is derived from a tricyclic [a.2.2.0$^{2,(a+1)}$]hydrocarbon, wherein a can in each case represent 3, 4, 5, 6 or 7.

In a further preferred embodiment the structure of the polyalicyclic structure element is derived from a tricyclic [a.3.1.1]hydrocarbon, wherein a can in each case represent 3, 4, 5, 6 or 7.

Insofar as a monomer according to the invention comprises two or a plurality of polyalicyclic structure elements Q, these can be identical or different.

Preference is for compounds according to the invention in which
(i) the structure element Z represents —O—(C=O)—C(CH$_3$)=CH$_2$, wherein the functional groups are allophanate, biuret or acyl urea groups, since with these compounds particularly good results have been obtained (see also examples),
and/or
(ii) the structure element Q represents a tricyclo[5.2.1.0$^{2,6}$] decane radical.

Greater preference is for compounds according to the invention, in which the structure element Z represents —O—(C=O)—C(CH$_3$)=CH$_2$, wherein the functional groups are allophanate, biuret or acyl urea groups and the structure element Q represents a tricyclo[5.2.1.0$^{2,6}$]decane radical.

Preference is for compounds according to the invention in which all photocurable groups present correspond to the structure element Z.

Preference is for compounds according to the invention in which all terminal polymerizable groups present correspond to the structure element Z.

A compound according to the invention, apart from photocurable groups of the structure element Z, can also comprise further polymerizable, preferably terminal polymerizable groups, which are not photocurable, in particular not under the normal conditions that exist in dentistry. This is generally not preferred, however, since such groups do not contribute towards the desired characteristics of the product that exists following polymerization.

Preferred compounds according to the invention comprise two, three, four or a plurality of functional groups selected from the group consisting of N-acyl urea, allophanate and biuret.

According to the invention compounds are preferred with one, two, three, four or a plurality of functional groups selected from the group consisting of N-acyl urea, allophanate and biuret.

The present invention also relates to a compound of structure $Q(YZ_e)_b$ with one, two, three, four or a plurality of functional groups that are selected from the group consisting of N-acyl urea, allophanate and biuret,
wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $YZ_e$ is or are substituted by alkyl groups, alkoxy groups, halogen atoms or trifluormethyl groups;

b is an integer selected from the group of integers 2, 3, 4;

each Z represents a structure element, which independently of any other structure elements Z is selected from the group consisting of

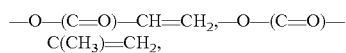

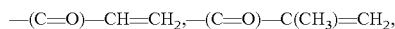

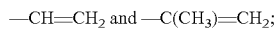

each index e is an integer, which independently of any further indices e is selected from the group of integers 1, 2, 3 and 4;

each Y represents a structure element that in the structure $Q(YZ_e)_b$ links the polyalicyclic structure element Q with e structure elements Z and contains or consists of a structure element selected from the group consisting of

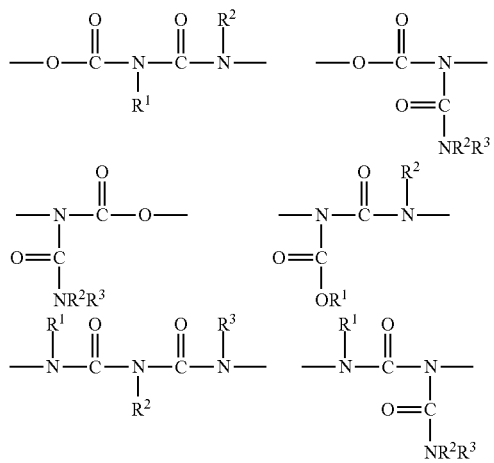

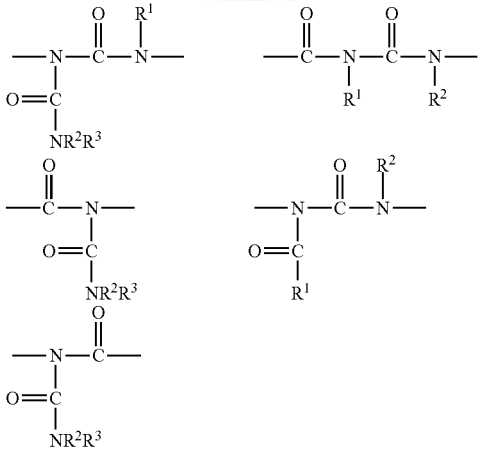

wherein $R^1$, $R^2$, and $R^3$ represent other radicals of the compound, wherein in each case the bond arranged to the left of the graphic formula is closer to the structure element Q and the bond arranged on the right is closer to the structure element Z.

Preferably such a compound according to the invention of structure $Q(YZ_e)_b$ comprises two, three, four or a plurality of functional groups selected from the group consisting of N-acyl urea, allophanate and biuret.

In a preferred configuration each index e represents an integer, which independently of any further indices e is selected from the group of integers 2, 3 and 4.

The abovementioned other radicals $R^1$, $R^2$ or $R^3$ of a compound according to the invention are, in each case independently of one another, preferably selected from the group consisting of hydrogen, linear, branched or ring-comprising structure elements with 1 through 30 C atoms and 0 through 10 heteroatoms, wherein the heteratoms that are optionally present are preferably selected from the group consisting of N and O.

The other radicals $R^1$, $R^2$ or $R^3$ of a compound according to the invention are, in each case independently of one another, preferably selected from the group consisting of hydrogen, linear, branched or ring-comprising structure elements with 1 through 25 C atoms and 0 through 8 heteroatoms, wherein the heteratoms that are optionally present are preferably selected from the group consisting of N and O.

The other radicals $R^1$, $R^2$ or $R^3$ of a compound according to the invention are, in each case independently of one another, preferably selected from the group consisting of hydrogen, linear, branched or ring-comprising structure elements with 1 through 20 C atoms and 0 through 5 heteroatoms, wherein the heteratoms that are optionally present are selected from the group consisting of N and O.

A compound according to the invention preferably is preparable by reacting a first reaction product, which is the reaction product of a first reaction of A) a compound of structure $QG_b$, in which each G represents a reactive group, which independently of other groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$
with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COOH,
wherein the following applies:
R in each case independently of any other R represents a hydrogen atom or an alkyl radical;
m is an integer selected from the group of integers from 0 through 10,
each index n is an integer, which independently of any other indices n is selected from the group consisting of 0 and 1,
wherein the compound is a second reaction product from a reaction of the above first reaction product with
C) a further compound according to A) or B), wherein each further compound according to A) or B) has the above meaning, independently of what A) and/or B) represent in the first reaction,
or
the compound is a third reaction product from a reaction of the above second reaction product with
D) a further compound according to A) or B), wherein each further compound according to A) or B) has the above meaning, independently of what A) and/or B) represent in the first and/or second reaction.

A compound according to the invention in a preferred configuration is a second reaction product from a reaction of the above first reaction product with
C) a further compound according to A) or B), wherein each further compound according to A) or B) has the same meaning as in the first reaction,
and/or
wherein the compound is a third reaction product from a reaction of the above second reaction product with
D) a further compound according to A) or B), wherein each further compound according to A) or B) has the same meaning as in the first and/or the second reaction, preferably as in the first and the second reaction.

In a first embodiment m=0. This applies to all aspects of the present invention.

In a preferred configuration a compound according to the invention (as defined above) comprises one or a plurality of structure elements selected from the group consisting of

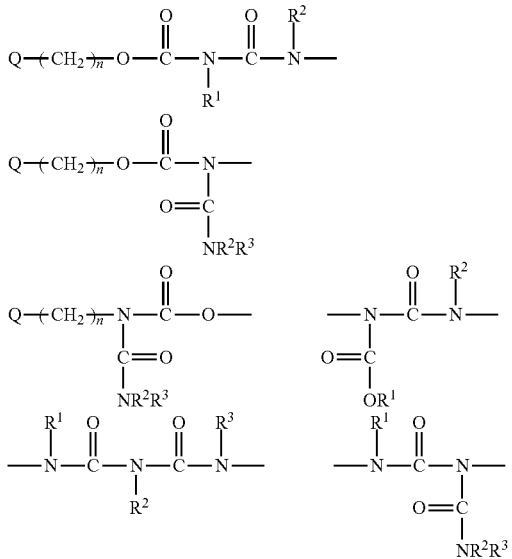

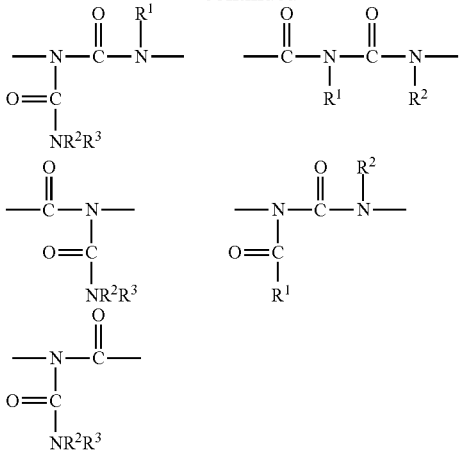

wherein $R^1$, $R^2$ and $R^3$ represent other radicals of the compound (and preferably have the abovementioned preferred meaning) and Q has the abovementioned meaning and the index n is selected from the group consisting of 0 and 1.

The bond shown on the right of each graphic formula is closest to the structure element Z.

Preferred compounds according to the invention are those wherein Q represents a polyalicyclic structure element, preferably a saturated polyalicyclic structure element, selected from the group consisting of bicyclic and tricyclic hydrocarbon radicals, wherein preferably none of the hydrogen atoms of this polyalicyclic structure element Q not substituted by substituents $YZ_e$ is substituted.

A preferred bicyclic hydrocarbon radical is a bicyclo [2.2.1]heptane radical, i.e. according to the invention compounds are preferred that have a bicyclo[2.2.1]heptane (norbornane).

In a further preferred embodiment the structure of the polyalicyclic structure element Q is derived from a tricyclodecane or tricyclodecene hydrocarbon.

Special preference is for monomers $Q(YZ_e)_b$ according to the invention whose polyalicyclic structure element Q is derived from one of the following tricyclic hydrocarbons: tricyclo[5.2.1.0$^{2,6}$]decane (TCD), tricyclo[5.2.1.0$^{2,6}$]dec-3-ene or tricyclo[3.3.1.1$^{3,7}$]decane (adamantane), i.e. preference is for compounds according to the invention, which have a TCD structure, a tricyclo[5.2.1.0$^{2,6}$]dec-3-ene structure or an adamantane structure.

Particularly preferred compounds according to the invention are those wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo [2.2.1]heptane radical.

The stated particularly preferred compounds according to the invention, in which the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo [2.2.1]heptane radical, are preferably those with a tricyclo [5.2.1.0$^{2,6}$]decane structure, a tricyclo[5.2.1.0$^{2,6}$]dec-3-ene structure, a tricyclo[3.3.1.1$^{3,7}$]decane structure or a bicyclo [2.2.1]heptane structure, in which none of the hydrogen atoms of this polyalicyclic structure element Q not substituted by substituents $YZ_e$ is substituted.

Particularly preferred compounds according to the invention are those wherein
A) a compound is of the structure $QG_b$, in which each G represents a reactive group, which independently of the other groups G is selected from the group consisting of —NH$_2$, —CH$_2$NH$_2$, —OH, —CH$_2$OH, —NCO, —CH$_2$NCO, and —COOH.

Further preferred compounds are those in which at least one structure element YZ$_e$ is selected independently of the further structure elements) YZ$_e$, and preferably all structure elements YZ$_e$ are selected from the group consisting of

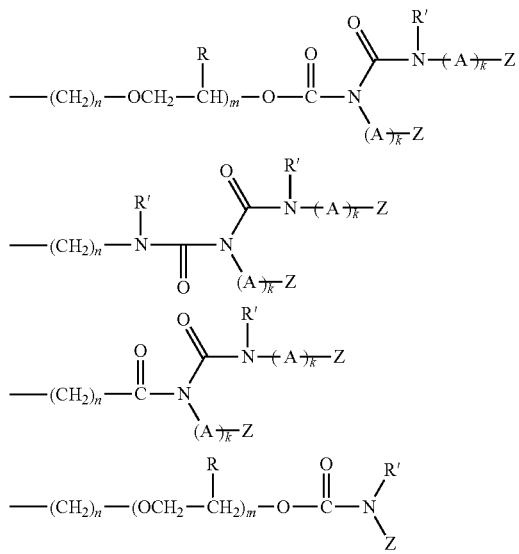

wherein Z, R, m and n have the meaning given above and wherein the following also applies:

each A represents a divalent organic bridge member, each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above.

Further preferred compounds are those where at least one structure element YZ$_e$ is selected independently of the further structure element(s) YZ$_e$, and preferably all structure elements YZ$_e$ are selected from the group consisting of

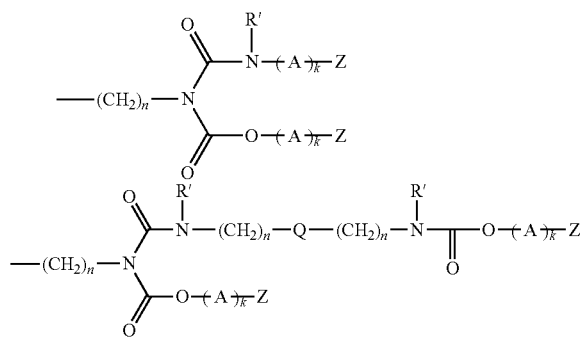

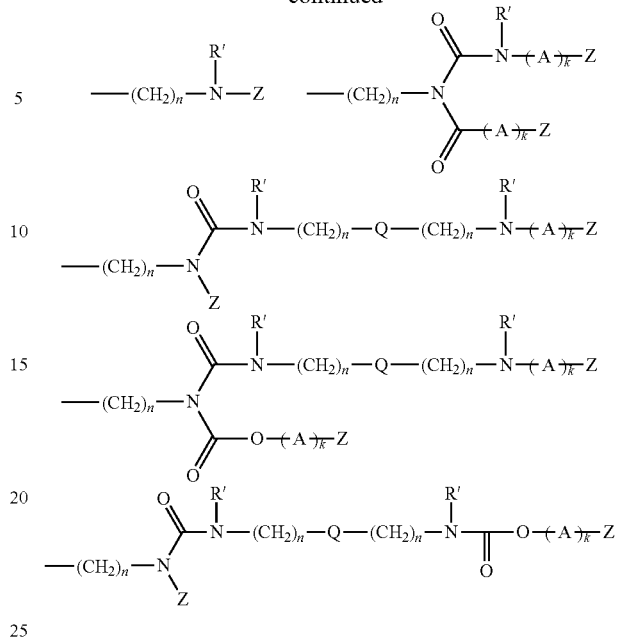

wherein each Q independently of any further structure elements Q has the above meaning and wherein Z, A, k and R', as well as n, have the above meaning.

Here in turn preference is for compounds in which each structure element A independently of any further structure elements A is selected from the group consisting of linear, branched or ring-comprising divalent organic bridge members with 1 through 25 C atoms and optionally 1 through 10, preferably 1 through 5 heteroatoms, wherein the heteroatoms that are optionally present are preferably selected from the group consisting of N and O.

Here in turn preference is for a compound according to the invention in which each structure element A independently of any further structure elements A is selected from the group consisting of linear, branched or ring-comprising structure elements with 1 through 25 C atoms and 0 through 10 heteroatoms, preferably with 1 through 5 heteroatoms, wherein the heteroatoms that are optionally present are preferably selected from the group consisting of N and O.

Further preference is for compounds in which each structure element A independently of any further structure elements A is selected from the group consisting of (C$_1$-C$_{20}$) alkylene, (C$_1$-C$_{20}$) heteroalkylene, (C$_3$-C$_{20}$) cycloalkylene, (C$_4$-C$_{20}$) cycloalkylalkyene, (C$_2$-C$_{20}$) alkenylene, (C$_3$-C$_{20}$) cycloalkenylene, CC$_4$-C$_{20}$) cycloalkenylalkylene, (C$_4$-C$_{20}$) cycloalkenylenalkylene, (C$_3$-C$_{25}$) arylene, (C$_2$-C$_{25}$) heteroarylene, (C$_4$-C$_{25}$) arylalkylene, C$_4$-C$_{25}$) arylenalkylene, (C$_4$-C$_{25}$) arylheteroalkylene, and (C$_4$-C$_{25}$) arylenheteroalkylene.

In preferred configurations structure element A comprises one or a plurality of the following atoms or groups of atoms:

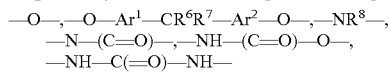

wherein the following applies:

Ar$^1$ and Ar$^2$ independently of each other represent an aromatic ring which is optionally substituted, here preferably once or a plurality of times substituted with C1-C4 alkyl radicals, here in turn preferably a phenyl ring, R$^6$, R$^7$ and R$^8$ independently of one another represent hydrogen or a C1-C8 radical, here preferably a C1-C4 alkyl radical, here in turn preferably methyl or ethyl.

For the preparation of the compounds according to the invention preferably hydroxyl compounds of (meth)acrylates can be used, wherein mixtures of acrylates and methacrylates can also be used. Preference for use as reaction partners according to components B), C) or D) is for:

alkylene oxide mono(meth)acrylates such as for example ethylene glycol mono(meth)acrylate, diethylene glycol mono (meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono (meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth) acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly($\epsilon$-caprolactone)mono(meth)acrylate, poly($\gamma$-caprolactone)mono(meth) acrylate, etc., the mono-, di-, tetra-, or penta(meth)acrylates of polyhydric alcohols, such as glycerin, such as for example glycerin di(meth)acrylate (2-hydroxypropyl-1,3-di(meth) acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth) acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth) acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

For the preparation of the compounds according to the invention as component B) isocyanates can also be used. Preference here is for mono- and diisocyanates.

Preferred diisocyanates are selected from the group consisting of cyclohexane diisocyanate, methylcyclohexane diisocyanate, ethylcyclohexane diisocyanate, propylcyclohexane diisocyanate, methyldiethylcyclohexane diisocyanate, phenylene diisocyanate, toluoylene diisocyanate, bis(isocyanatophenyl)methane, propane diisocyanate, butane diisocyanate, pentane diisocyanate, hexane diisocyanate, such as hexamethylene diisocyanate or 1,5-diisocyanato-2-methyl pentane, heptane diisocyanate, octane diisocyanate, nonane diisocyanate, such as 1,6-diisocyanato-2,4,4-trimethylhexane or 1,6-diisocyanato-2,2,4-trimethylhexane, nonane triisocyanate, such as 4-isocyanatomethyl-1,8-octane diisocyanate, decane di- and triisocyanate, undecane di- and -triisocyanate, dodecandi- and -triisocyanates, isophorone diisocyanate, dicyclohexylmethane-4,4'-diisocyanate, isocyanatomethylmethylcyclohexyl isocyanate, 1,3-bis(isocyanatomethyl)cyclohexane or 1,4-bis(isocyanatomethyl) cyclohexane.

Preferred monoisocyanates are (meth)acryloyl isocyanate and (meth)acryl-C2-C8-alkyl isocyanates (e.g. (meth)acrylalkyl isocyanates with alkyl spacers, having 2 through 8, in particular preferably 2 through 6 carbon atoms), here in turn preference is for (meth)acryl ethyl isocyanate (2-isocyanatoethyl(meth)acrylate).

Furthermore, as component B) monoisocyanates have proven to be an advantage that are the reaction products of amino- or hydroxyalkyl(meth)acrylates, the alkyl spacers of which have 1 through 12, preferably 2 through 8, in particular preferred 2 through 6 carbon atoms, and diisocyanates.

Preferably to this end a diisocyanate mentioned above is reacted in equimolar proportions with an amino- or hydroxylalkyl compound (indicated above as preferred) of a (meth) acrylate, wherein the hydroxyalkyl compounds in turn are preferably selected from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Quoted examples are the reaction products in the molar ratio of 1:1 of hydroxyethylmethacrylate and isophorone diisocyanate, dicyclohexylmethane-4,4'-diisocyanate or hexamethylene diisocyanate.

A preferred method according to the invention for preparation of a compound $Q(YZ_e)_b$, preferably in one of the abovementioned preferred or particularly preferred configurations, or a mixture comprising at least one compound $Q(YZ_e)_b$, is a method with the following steps:

In a first reaction, reacting

A) a compound of structure $QG_b$, in which each G represents a reactive group, which independently of further groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$ with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COOH to form a first reaction product, in a second reaction, reacting the first reaction product with C) a further compound according to A) or B), wherein each further compound according to A) or B) has the above meaning, independently of what A) and/or B) represent in the first reaction, to form a second reaction product, and optionally in a third reaction, reacting the second reaction product with D) a further compound according to A) or B), wherein each further compound according to A) or B) has the above meaning, independently of what A) and/or B) represent in the first and/or second reaction.

wherein Q, b, Y, Z, e, M, R, m and n in each case have the above meanings, and wherein the ratio of the total number of NCO groups to the total number of —NH$_2$, —OH and —COOH in the total number of compounds according to A) and B) in the first, the second and optional third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

In a method according to the invention for the preparation of a compound $Q(YZ_e)_b$ according to the invention the ratio of the total number of NCO groups reacted to the total number of —NH$_2$, —OH and —COOH reacted in the total number of compounds according to A) and B) in the first, (optional) second and optional third reaction is preferably in the range 1.1:1 through 5:1, more preferably in the range 1.25:1 through 4:1, in particular preferably in the range 1.5:1 through 3:1, and most preferably in the range 2:1 through 2.5:1.

Preferably the reaction to the first reaction product, to the second reaction product and/or to the third reaction product takes place in the presence of a catalyst.

Preferred catalysts here are tertiary amines or Lewis acids, here in turn preference is for metal salts of higher fatty acids, in particular dibutyltin dilaurate or tin (II) octoate.

The quantity of catalyst here is preferably in the range 0.01 through 2 wt. %, preferably 0.08 through 1 wt. %, in relation to the total quantity of reactants according to A) and B) and optionally C) and optionally D).

The reaction to the first reaction product, to the second reaction product and/or the third reaction product preferably takes place in a temperature range of 0 through 160° C., preferably in the range 30 through 140° C. and particularly preferably in the range 60 through 120° C. The reaction is preferably carried out at normal pressure (1013 mbar).

The configurations above or below concerning the compounds according to the invention identified as preferred and particularly preferred apply to the preferred and particularly preferred configurations of the method, mixtures, composites, products and applications according to the invention accordingly in each case.

In a further aspect the present invention relates to a mixture comprising one, two or a plurality of different compounds according to the invention (preferably in one of the configurations identified as preferred or particularly preferred), that can prepared using a method according to the invention (preferably in one of the configurations identified as preferred or particularly preferred).

In a further aspect the present invention relates to a curable blend, comprising
(a) one or a plurality of compounds according to the invention (preferably in one of the configurations identified as preferred or particularly preferred) or a mixture according to the invention (preferably in one of the configurations identified as preferred or particularly preferred),
and
(b) one or a plurality of further components selected from the group consisting of
  (b-1) monomers differing from constituent (a), which are copolymerizable with component (a), preferably photopolymerizable monomers, preferably selected from the group consisting of acrylates and methacrylates,
  (b-2) one or a plurality of fillers, preferably one or a plurality of nanoscale fillers,
  (b-3) photoinitiators and initiators for the chemical curing
  (b-4) polymerization inhibitors,
  and
  (b-5) solvents.

A preferred blend according to the invention relates to a chemically and/or light-induced or heat-induced curing dental composition.

Constituent (b-1) Polymerizable Monomers

The polymerizable monomers are preferably radically photopolymerizable monomers, preferably substances having one, two or a plurality of ethylenic groups such as for example, but without being limited to, the (meth)acrylate monomers commonly used in dental chemistry.

The patent literature mentions a number of other compounds (for example also in DE 3941629 A1, which by way of reference is a constituent of this application), which are all diesters of acrylic or methacrylic acid and are suitable for use in a curable blend according to the invention.

In a preferred curable blend according to the invention constituent (b-1) contains one or a plurality of dimethacrylate monomers selected from the group consisting of ethylene glycol dimethacrylate, 1,6-hexanediol dimethacrylate (HEDMA), triethylene glycol dimethacrylate (TEDMA), 1,12-dodecanediol dimethacrylate, ethoxylated bisphenol A dimethacrylate, polyethylene glycol dimethacrylate, 7,7,9-trimethyl-4,13-dioxo-5,12-diazahexadecane-1,16-dioxy-dimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, glycerin dimethacrylate, bisphenol A glycidyl methacrylate (bis-GMA) and dimethacrylates of dihydroxymethyltricyclo[$5.2.1.0^{2,6}$]decane.

The radical photopolymerizable monomers can also be hydroxyl compounds with at least one ethylenic double bond. Here preferably the hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerin dimethacrylate, and 2,2-bis[4-[3-methacryloyloxy-2-hydroxypropoxy]phenyl]propane.

Photocurable monomers with ethylenic double bonds based on polysiloxanes as for example described in DE 199 03 177 or in DE 44 16 857, which by way of reference are a constituent of this application, can also be used.

Further, so-called ormocers, which will be known to persons skilled in the art and which are for example described in DE 199 03 177 or in DE 44 16 857, which by way of reference are a constituent of this application, can be used.

Constituent (b-2) Fillers

As constituent (b-2) organic and/or inorganic fillers can be used.

Inorganic fillers can be used alone or in mixtures. In order to optimize the product features the inorganic fillers can be introduced into the formulations in varying grain sizes. The fillers can have a unimodal or polymodal, for example a bimodal, distribution.

The average particle size $d_{50}$ of the filler particles to be used according to the invention of the filler constituent (b-2) of a mixture according to the invention is determined by means of light scattering (laser diffraction), preferably with a Beckman Coulter LS 13320 particle size analyzer.

Compact glasses and various silicic acids in different sizes and states (monodisperse, polydisperse) are used as inorganic fillers.

Suitable inorganic constituents are for example amorphous materials with a mixed oxide base of $SiO_2$, $ZrO_2$ and/or $TiO_2$, microfine fillers such as pyrogenic silicic acid or precipitated silicic acid and macro- or mini-fillers such as quartz-glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zircon mineral, hardly soluble metal salts such as barium sulfate or calcium fluoride and X-ray opaque fillers such as ytterbium fluoride.

For a better assembly of the polymer matrix the fillers can be surface modified. One example of surface treatment of the fillers is the use of a silane. Methacryloxypropyltrimethoxysilane is particularly well-suited as a bonding agent.

In order to adjust the rheology curable blends and products according to the invention can contain various silicic acids, preferably pyrogenic silicic acids.

In addition materials with a strengthening effect such as glass fibers, polyamide or carbon fibers can be used. The curable blends and products according to the invention can also contain fine particle splinters or bead polymers, wherein the bead polymers can be homo- or copolymers or organically curable monomers.

Preferably the curable blends and products according to the invention, in particular for use in dentistry, contain nanoscale solid particles. Nanoscale solid particles are particles with an average particle size of more than 200 nm, preferably not more than 100 nm and in particular not more than 70 nm. The nanoscale inorganic solid particles are preferably those of metal oxides, sulfides, selenides and tellurides and mixtures of these. Particularly preferred are nanoscale particles of $SiO_2$, $TiO_2$, $ZrO_2$, ZnO, $SnO_2$ and $Al_2O_3$ and mixtures of these. The preparation of nanoscale solid particles takes place in ways that are known, e.g. by flame pyrolysis, the plasma method, gas-phase condensation, colloidal techniques, precipitation methods, sol-gel method, and so on. Organically surface-modified nanoscale inorganic solid particles are preferred. The organic surface modification improves the bonding of the nanoscale particles in the polymer matrix.

In a preferred configuration the nanoscale particles are present in non-agglomerated form, for example dispersed in a medium, in particle in monodisperse form.

In order to allow the nanoparticles to achieve a proper bonding in the polymer matrix of a curable blend or product according to the invention, the surfaces of the nanoparticles (preferably the preferred oxidic nanoparticles) are organically modified, i.e. their surfaces have organic structure elements. One example of surface treatment of the fillers is the use of a silane, leading to the formation of silanized nanoparticles. Methacryloxypropyltrimethoxysilane is particularly well-suited as a bonding agent.

In a further preferred configuration the nanoscale particles are non-agglomerated, organically surface-modified nanoparticles with an average particle size of less than 200 nm, preferably less than 100 nm, particularly preferably less than 60 mm, which in turn are preferably silanized.

Constituent (b-3)—Photoinitiators

Examples of a photoinitiator include catalysts which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019 092 A1 or in DE 39 41 629 C2, which by way of reference are a constituent of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 A1 or in DE 39 41 629 C2, which by way of reference are a constituent of this application.

Further suitable initiators and initiator combinations are described in DE 601 16 142, which by way of reference are a constituent of this application.

The photoinitiators used in connection with the present invention are characterized in that through the absorption of light in the wavelength range 300 nm through 700 nm, preferably 350 nm through 600 nm and particularly preferably 380 through 500 nm, optionally in combination with a number of co-initiators, they can bring about the curing of a mixture that is curable according to the invention.

The absorption maximum of campherquinone (CQ) is approximately 470 nm and thus in the range of blue light. Campherquinone (CQ) is one of the $PI_2$-initiators and is regularly used together with a co-initiator.

A curable blend according to the invention preferably contains a combination of an alpha-diketone and an aromatic tertiary amine, preferably the combination is of campherquinone (CQ) and ethyl-p-N,N-dimethylaminobenzoate (DABE).

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide. Regarding the structures of suitable phosphine oxides for use in a curable blend according to the invention reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a constituent of this application.

The phosphine oxides indicated in these printed publications are particularly suitable on their own or in combination with the "alpha-diketone/amine" system as a photopolymerization initiator system in the mixtures according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a constituent of this application.

Constituent (b-3)—Initiators for the Chemical Curing

Various initiators for a chemical curing will be known to a person skilled in the art. In this connection reference is made by way of example to EP 1 720 506.

Preferred initiators for chemical curing are benzoyl peroxide, lauroyl peroxide in particular dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 14 95 520, WO 02/092021 or in WO 02/092023, which by way of reference are a constituent of this application.

Suitable malonyl sulfamides are described in EP 0 059 451 which by way of reference is a component part of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2,6,6-diocytyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper naphthenate.

Constituent (b-4)—Polymerization Inhibitors

The curable blends according to the invention preferably contain one or a plurality of inhibitors, also referred to as stabilizers. These are added to a curable blend in order to prevent spontaneous polymerization. They react with prematurely forming radicals, which are intercepted, prevent premature polymerization and increase the storage stability of the curable, in particular photocurable, dental blend. Common inhibitors are phenol derivates such as hydroquinone monomethylether (HOME) or 2,6-di-tert.butyl-4-methylphenol (BHT). Further inhibitors such as 2,2 diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1 which by way of reference are a constituent of this application. Alternative inhibitors are indicated in DE 101 19 831 A1 or in EP 1 563 821 A1, which by way of reference are a component part of this application.

Constituent (b-5)—Solvents

The solvents are those commonly used in the coatings industry, such as for example hydrocarbons, ketones and esters such as for example toluene, xylene, isooctane, acetone, butanone, methyl isobutyl ketone, ethyl acetate, butyl acetate, tetrahydrofuran, N-methylpyrrolidone, dimethyl acetamide and dimethyl formamide. Alcohols can also be used such as ethanol, propanols, butanols, pentanols, hexanols, cyclohexanol, heptanols, octanols, nonanols, decanols, etc. Also suitable are cycloaliphatic or arylaliphatic alcohols.

In the following the invention is initially explained in detail for monomers comprising tricyclic structure elements Q using the example of tricyclo[5.2.1.0$^{2,6}$]decane (TCD)-derivatives.

1.) Starting with the bis(hydroxymethyl)tricyclo[5.2.1.0$^{2,6}$]decane (TCD-diol)

bis(hydroxymethyl)tricyclo[5.2.1.0$^{2,6}$]decane is commercially available, for example as a dicidol mixture of the isomeric compounds 3,8-bis(hydroxymethyl)tricyclo[5.2.1.0$^{2,6}$]decane and 4,8-bis(hydroxymethyl)tricyclo[5.2.1.0$^{2,6}$]decane as well as 3,9-bis(hydroxymethyl)tricyclo[5.2.1.0$^{2,6}$]decane and 4,9-bis(hydroxymethyl)tricyclo[5.2.1.0$^{2,6}$]decane.

The bis(hydroxymethyl)tricyclo[5.2.1.0$^{2,6}$]decanes can, starting with dicyclopentadiene (tricyclo[5.2.1.0$^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[5.2.1.0$^{2,6}$]decane. According to the synthesis route taken bis(hydroxymethyl)tricyclo[5.2.1.0$^{2,6}$]decanes specifically substituted at different positions can be obtained. Thus in published documents JP 7-206740, EP 1 112 995 B1 or EP 0 049 631 B1 specifications are provided on how, for example, the 8,9-bis(hydroxymethyl)tricyclo[5.2.1.0$^{2,6}$]decane can be prepared. DE 103 52 260 B3 on the other hand describes a method for preparing 3(4), 8(9)-bis(hydroxymethyl)tricyclo[5.2.1.0$^{2,6}$]decane. The notation of the positions of the hydroxymethyl groups 3(4), 8(9) means 3 or 4, 8 or 9.

The commercially available starting compound that can be used for the preparation of monomers according to the invention, bis(hydroxymethyl)tricyclo[5.2.1.0$^{2,6}$]decane, thus contains hydroxymethyl groups both at positions 3 or 4 and in positions 8 or 9. It is now possible by addition of alkylene oxides, in general in quantities of 1 through 10 mol, in particular of ethylene oxide, propylene oxide, butylene oxide, etc. in the presence of basic catalysts and according to known methods to synthesize the corresponding polyether polyols. EP0023686 B1 contains more detailed preparation specifications in this connection.

The reaction of the 3(4), 8(9)-bis(hydroxymethyl)tricyclo[5.2.1.0$^{2,6}$]decanes with isocyanates to form the corresponding urethanes is likewise known. Thus DE 35 22 006 A1 describes the reaction of the 3(4), 8(9)-bis(hydroxymethyl)tricyclo[5.2.1.0$^{2,6}$]decane with 2-isocyanatoethyl methacrylate. 2-isocyanatoethyl methacrylate is commercially available or can be synthesized according to the preparation specification from DE 33 38 077 A1 by phosgenation of dihydrooxazines.

The reaction product obtained (Formula (1)) of 2-isocyanatoethyl methacrylate with 3(4), 8(9)-bis(hydroxymethyl)tricyclo[5.2.1.0$^{2,6}$]decane in a formulation following curing has a lower reaction shrinkage and a high mechanical strength.

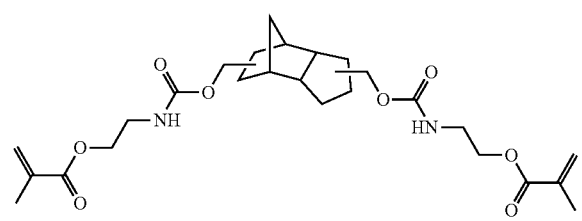

Formula (1)

The urethane of Formula (1) still has two hydrogen atoms capable of reacting with nitrogen, which now in a second reaction stage are further reacted with excess isocyanate to form a compound according to the invention. In the process the allophanate of Formula (2) initially forms as a tetrafunctionalized radically cross-linkable compound. In turn this monomer also still has hydrogen atoms capable of reacting with nitrogen, which according to the invention when reacting with further isocyanate form the hexafunctionalized, radically curable allophanate of Formula (3).

Formula (2)

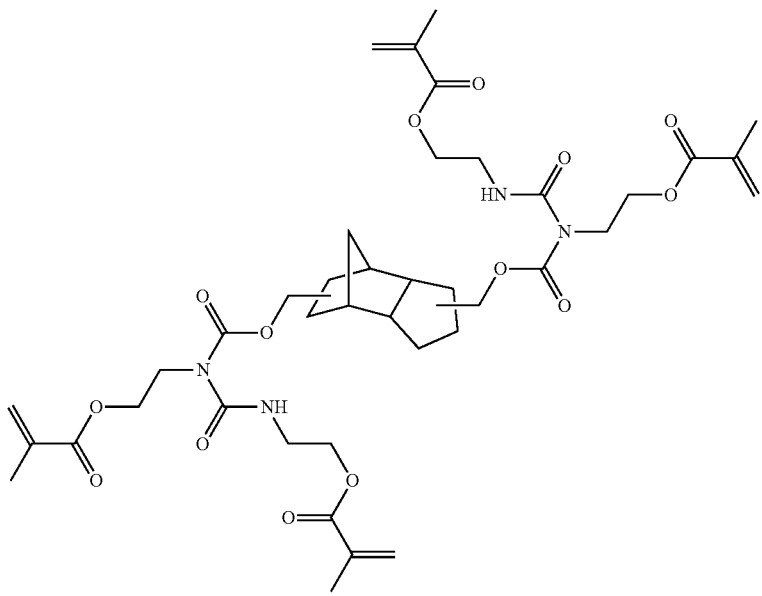

Formula (3)

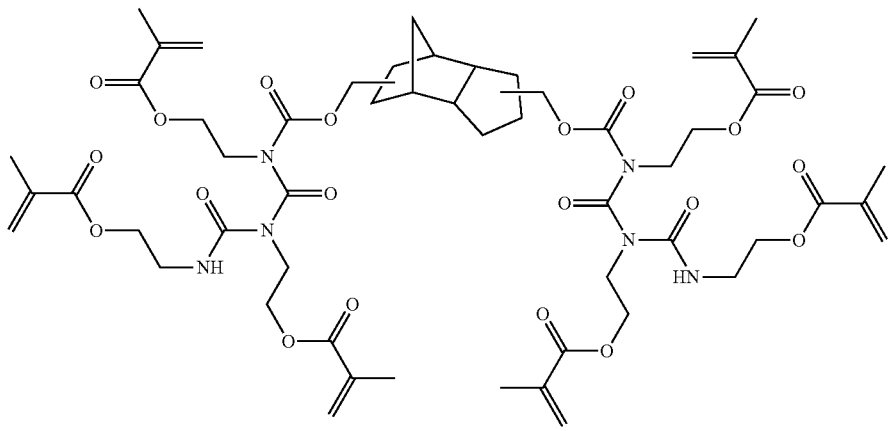

Alternatively the 3(4), 8(9)-bis(hydroxymethyl)tricyclo [5.2.1.0$^{2,6}$]decane can also be brought into a reaction with methacryloyl isocyanate. Methacryloyl isocyanate is commercially available or can be obtained by reacting methacrylamide with oxalyl chloride, as described in EP 0 143 613 B1. In the reaction the 2-isopropenyloxazoline-4,5-dione-hydrochloride is formed first, which then results in the methacryloyl isocyanate through decomposition. Experimental data on this point can be found in EP 0 202 840. Through the reaction of 3(4), 8(9)-bis(hydroxymethyl)tricyclo[5.2.1.0$^{2,6}$]decane also with methacryloyl isocyanate a compound of Formula (4) is obtained:

Formula (4)

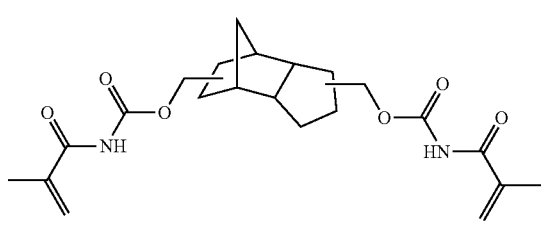

The remaining hydrogen atoms able to react with nitrogen of the compound of Formula (4) can then in turn be reacted in isocyanate reactions to form the allophanates. The reaction products with 2-isocyanatoethyl methacrylate (Formula (5)) and methacryloyl isocyanate (Formula (6)) are shown here as an example.

Formula (5)

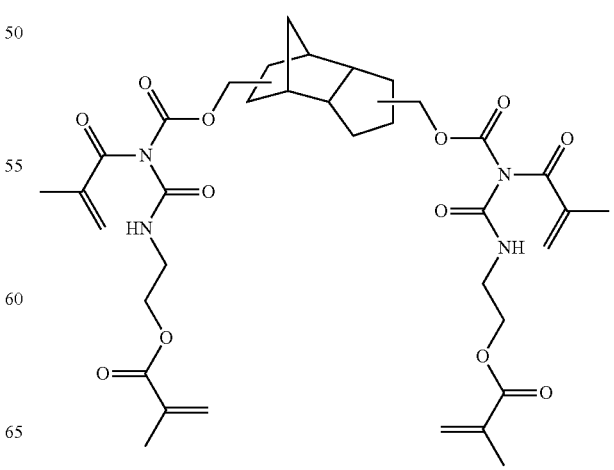

Formula (6)
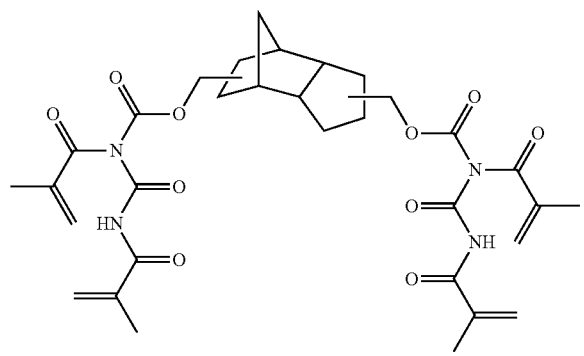
If 1,6-hexane diisocyanate is reacted with an equivalent 2-hydroxyethyl methacrylate, a urethane is obtained.
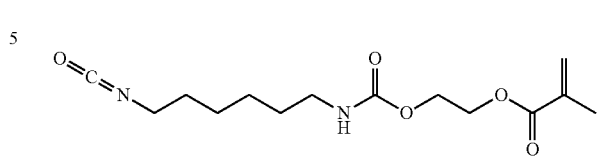
Because of the remaining isocyanate functionality, this can be reacted with 3(4), 8(9)-bis(hydroxymethyl)tricyclo[5.2.1.0$^{2,6}$]decane to form the allophanate (Formula 7) shown below.
Formula (7)
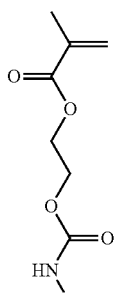
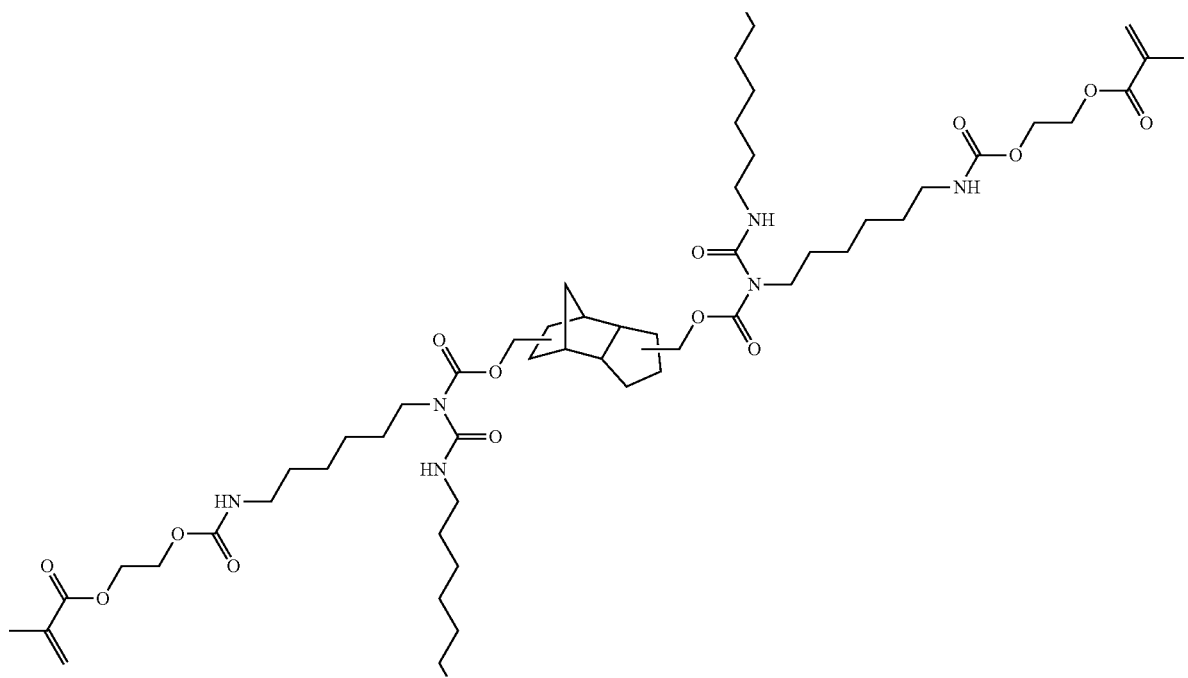

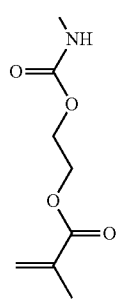

Instead of 1,6-hexane diisocyanate, methane diphenyl diisocyanate or isophorone diisocyanate could be used.

The hydrogen atoms that can still react with nitrogen can be further reacted in reactions with isocyanate groups.

2.) Starting with 3(4), 8(9)-bis(carboxylic acid)tricyclo[5.2.1.0$^{2,6}$]decane The 3(4), 8(9)-bis(carboxylic acid)tricyclo[5.2.1.0$^{2,6}$]decane is preparable by simple oxidation of the commercially available 3(4), 8(9)-bis(formyl)tricyclo[5.2.1.0$^{2,6}$]decane.

Reaction of the dicarboxylic acid with 2-isocyanatoethyl methacrylate produces the amide of Formula (8):

Formula (8)

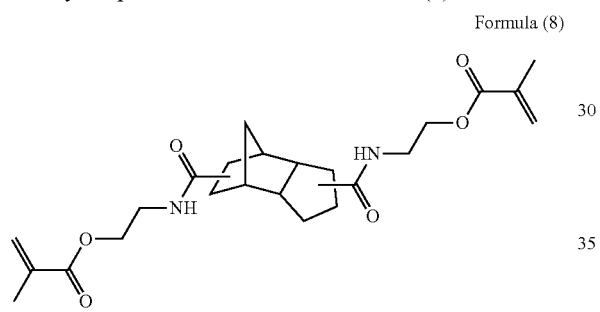

Further reaction of the two amide-hydrogen atoms of the amide of Formula (8) capable of reacting with 2-isocyanatoethyl methacrylate produces the acyl urea of Formula (9).

Formula (9)

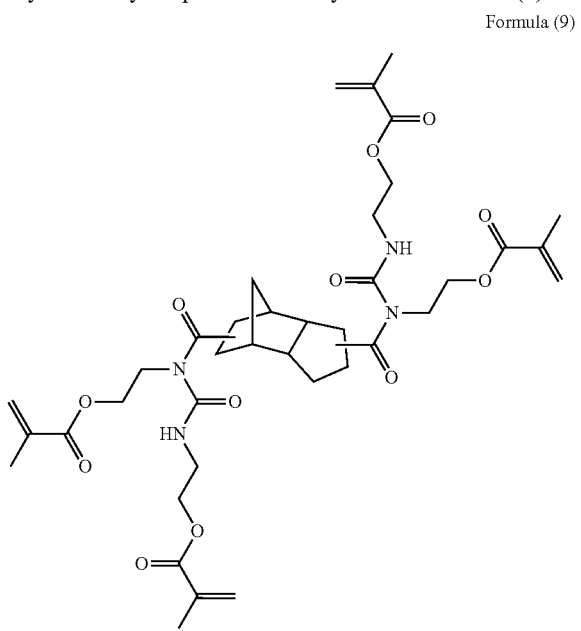

If 3(4), 8(9)-bis(carboxylic acid)tricyclo[5.2.1.0$^{2,6}$]decane is reacted with methacryloyl isocyanate, the imide of Formula (10) results. The hydrogen atoms that react with nitrogen can here also be further reacted in isocyanate reactions.

Formula (10)

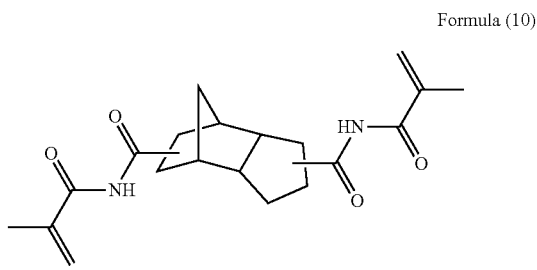

3.) Starting with 3(4), 8(9)-bis(isocyanatomethyl)tricyclo[5.2.1.0$^{2,6}$]decane The 3(4), 8(9)-bis(isocyanatomethyl)tricyclo[5.2.1.0$^{2,6}$]decane is in itself known and is one of the diisocyanate compounds commonly used in industrial applications (see DE 37 03 120 A1 and WO 2009/065873 A2). The conducting according to the invention of the second reaction stage of the isocyanate-alcohol reaction can be initiated not only starting with tricyclodecandiol and the isocyanatoethyl methacrylate, but also starting with the tricyclodecane diisocyanate and hydroxyethyl methacrylate. Through stoichiometric reaction of the two reactants the urethane of Formula (11) is obtained.

Formula (11)

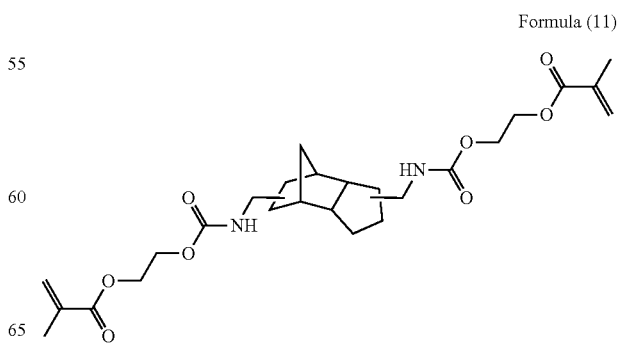

This carbamate (Formula (11)) also has two hydrogen atoms capable of reacting with nitrogen, which can be further reacted with an excess of bis(isocyanatomethyl)tricyclo [5.2.1.0$^{2,6}$]decane to form the diisocyanate of Formula (12).
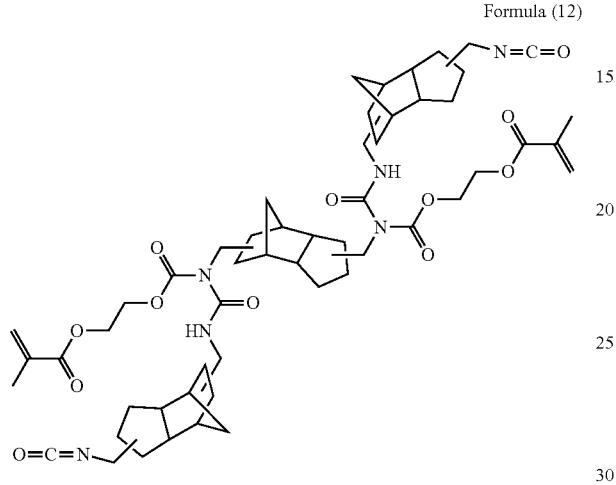
Formula (12)
Reaction of the allophanate diisocyanate (Formula 12) with methacrylic acid produces the compound of Formula (13).
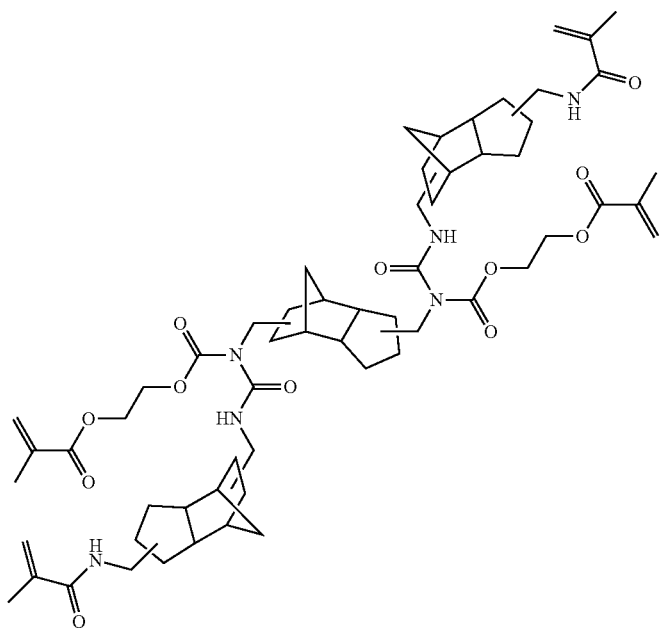
Formula (13)

Alternatively, the urethane of Formula (11) in the second reaction stage can be reacted with 2-isocyanatoethyl methacrylate also to form the allophanate of Formula (14).
Formula (14)
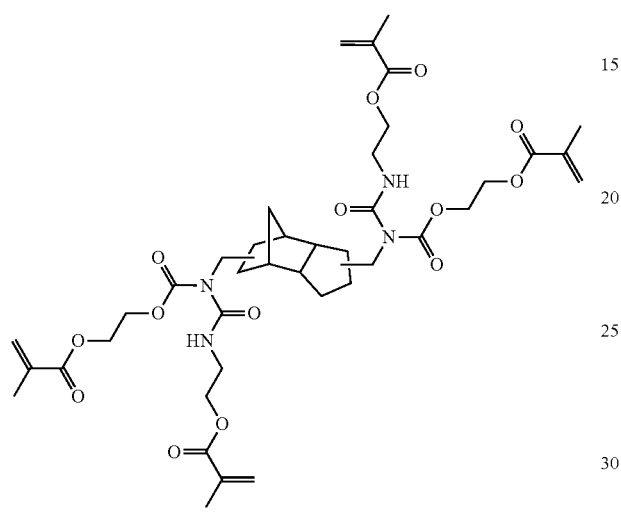
The diisocyanate groups of the compound of Formula (12) can further be reacted with stoichiometric quantities for example of hydroxyethyl methacrylate to form the compound of Formula (15).
Formula (15)
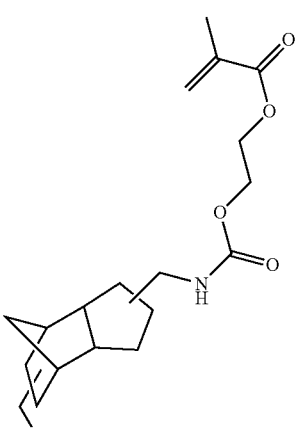

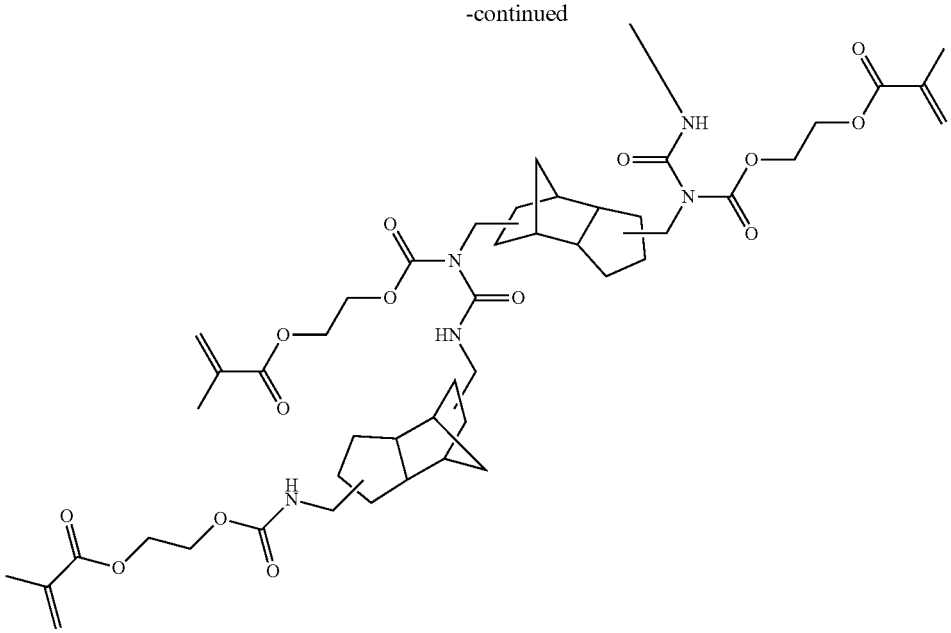

Instead of hydroxyethyl methacrylate in the reactions described by way of example above other hydroxyl compounds of (meth)acrylates can be used, wherein mixtures of acrylates and methacrylates can also be used. So—analogously to the above example—3(4), 8(9)-bis(isocyanatomethyl)tricyclo[5.2.1.0$^{2,6}$]decane can be reacted. Here, preferred hydroxyl compounds of (meth)acrylates are.

Alkylene oxide mono(meth)acrylates such as for example ethylene glycol mono(meth)acrylate, diethylene glycol mono (meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono (meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly(ε-caprolactone)mono(meth)acrylate, poly(γ-caprolactone)mono(meth) acrylate, etc., the mono-, di-, tetra-, or penta(meth)acrylates of polyhydric alcohols, such as glycerin, such as for example glycerin di(meth)acrylate (2-hydroxypropyl-1,3-di(meth) acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth) acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth) acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

All these compounds have both (meth)acrylate groups and hydroxy groups. The latter can react with isocyanate groups in the manner described above for the reaction between hydroxyethyl methacrylate and 3(4), 8(9)-bis(isocyanatomethyl)-tricyclo[5.2.1.0$^{2,6}$]decane. Thus in a single reaction step a high degree of functionalization can be achieved.

3(4), 8(9)-bis(isocyanatomethyl)tricyclo[5.2.1.0$^{2,6}$]decane can be reacted with 2-carboxylic acid-methacrylate to form the corresponding amide of Formula (16).

Formula (16)

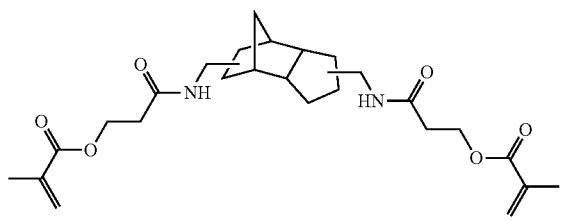

Reacting of the amide of Formula (16) with 2-isocyanatoethyl methacrylate produces the acyl urea of Formula (17).

Formula (17)

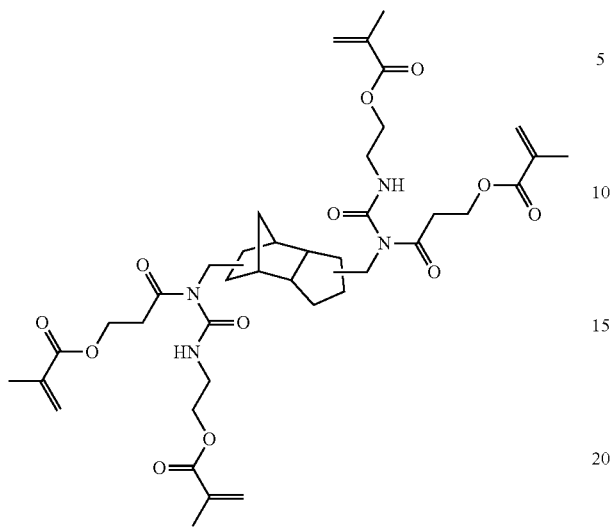

The amide of Formula (16) can also be reacted with an excess of 3(4), 8(9)-bis(isocyanatomethyl)tricyclo[5.2.1.0$^{2,6}$]decane to form the corresponding isocyanate, wherein the isocyanate so formed is further reacted with hydroxyethyl methacrylate to form the cross-linkable monomer of Formula (18).

Formula (18)

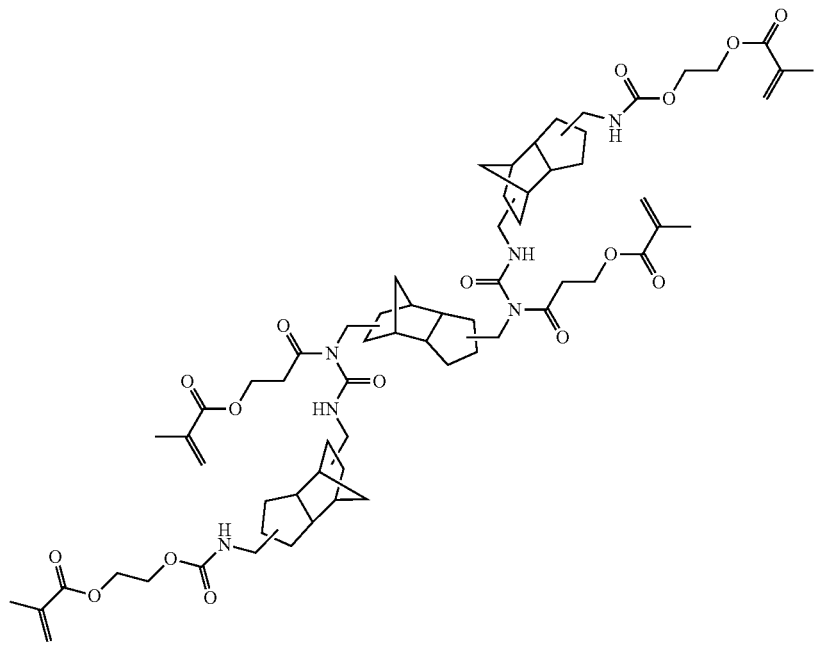

If 3(4), 8(9)-bis(isocyanatomethyl)tricyclo[5.2.1.0$^{2,6}$]decane is reacted with 2-methacryloyloxy ethyl hydrogen succinate, then the amide of Formula (19) is obtained, which is further reacted with 2-isocyanatoethyl methacrylate to form the acyl urea of Formula (20).

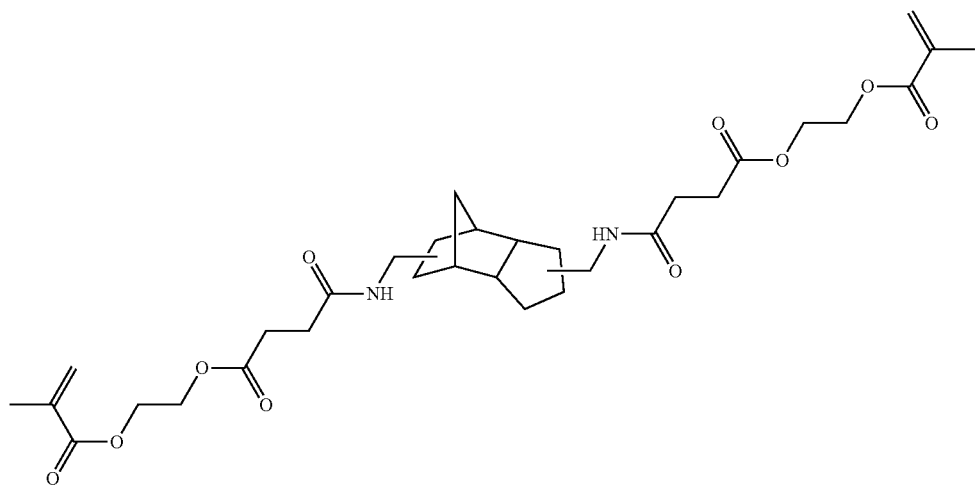

Formula (19)

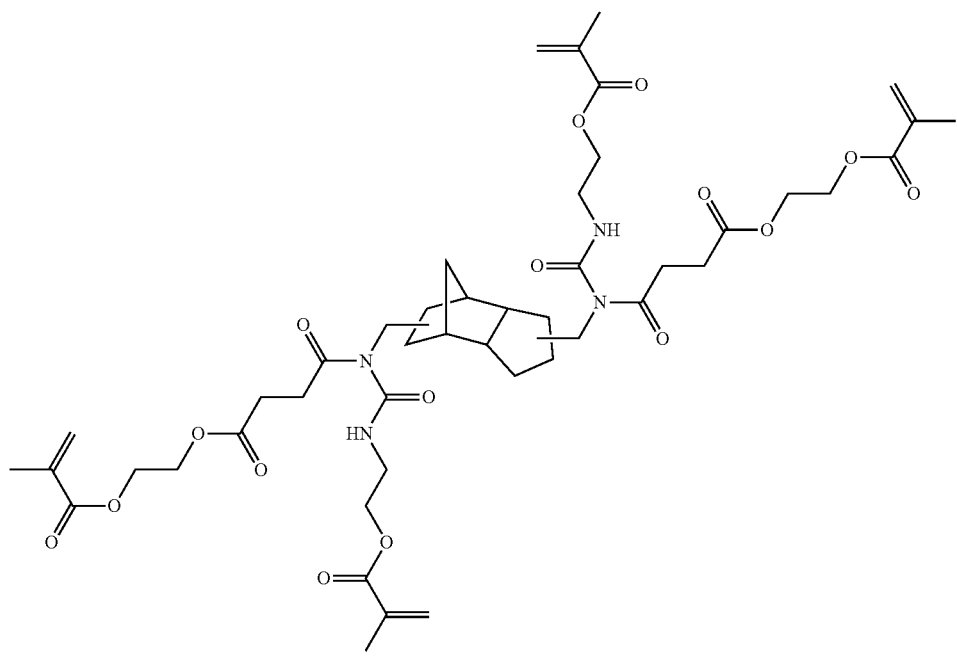

Formula (20)

Further suitable carboxylic acid methacrylates can be obtained from reactions between di- or tetracarboxylic acid mono- or dianhydride with suitable OH-functionalized, curable compounds such as for example 2-hydroxyethyl methacrylate.

From the reaction of the 3(4), 8(9)-Bis(isocyanatomethyl) tricyclo[$5.2.1.0^{2,6}$]decane with methacrylic acid after subsequent decarboxylation the amide of Formula (21) results.

Formula (21)
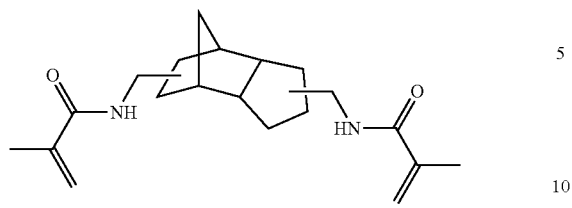
From the amide of Formula (21) through further reaction of the NH functionality with 2-isocyanatoethyl methacrylate the tetrafunctionalized monomer of Formula (22), which is a cross-linker, results.
Formula (22)
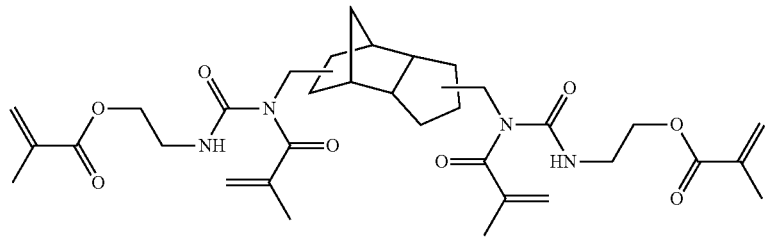
If the amide of Formula (21) is reacted with a plurality of 3(4), 8(9)-bis(carboxylic acid)tricyclo[5.2.1.0$^{2,6}$]decane, the diisocyanate of Formula (23) results.
Formula (23)
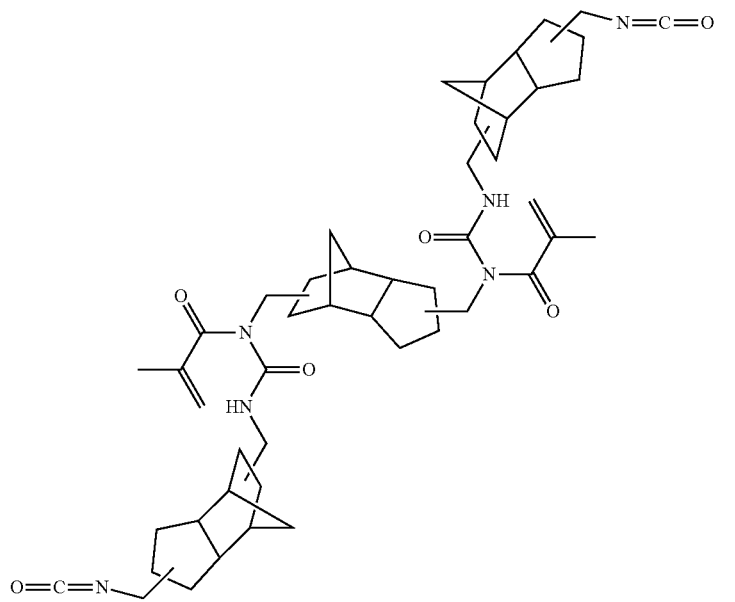

The diisocyanate of Formula (23) can be reacted with two further equivalent methacrylic acids to form the compound of Formula (24).
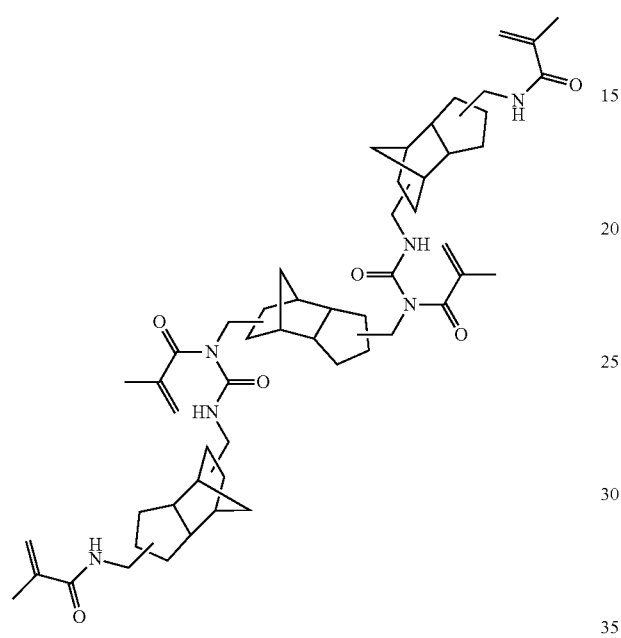
Formula (24)
The reaction of the diisocyanate of Formula (23) with 2-hydroxyethyl methacrylate results in the compound of Formula (25).
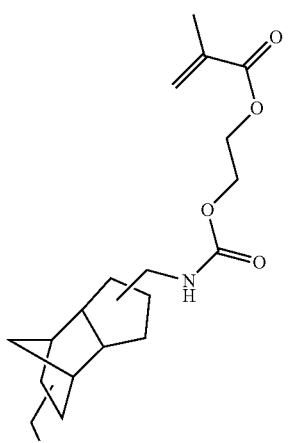
Formula (25)

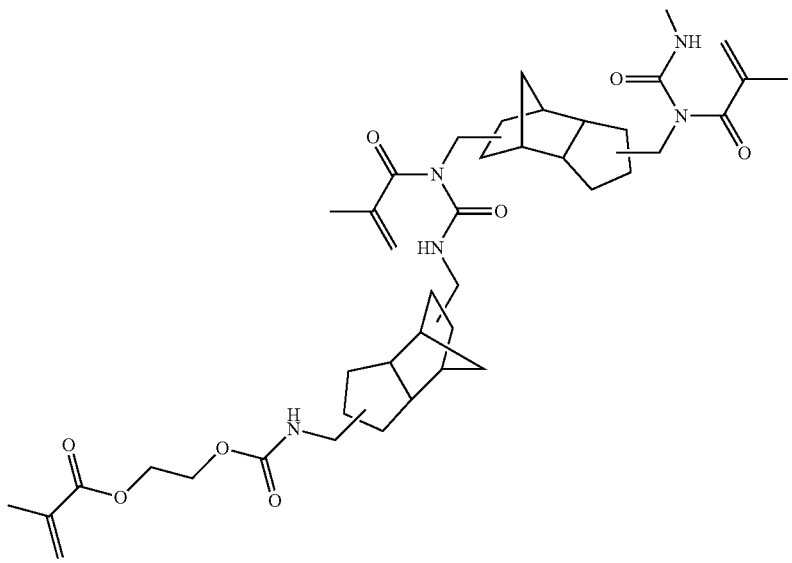

4.) Starting with 3(4), 8(9)-bis(aminomethyl)tricyclo[5.2.1.0²,⁶]decane

The 3(4), 8(9)-bis(aminomethyl)tricyclo[5.2.1.0²,⁶]decane is in itself known or can be prepared for example by reaction of the corresponding tosylates with ammonia. Reaction of the 3(4), 8(9)-bis(aminomethyl)tricyclo[5.2.1.0²,⁶]decane with 2-isocyanatoethyl methacrylate results in the urea compound of Formula (26) known from EP 0 209 700 A2.

The 3(4), 8(9)-bis(aminomethyl)tricyclo[5.2.1.0²,⁶]decane can also be brought into a reaction with methacryloyl isocyanate to form the corresponding acyl urea. The further reaction of the remaining hydrogen atoms reactive to nitrogen with methacryloyl to isocyanate provides the biuret of Formula (28).

Formula (26)

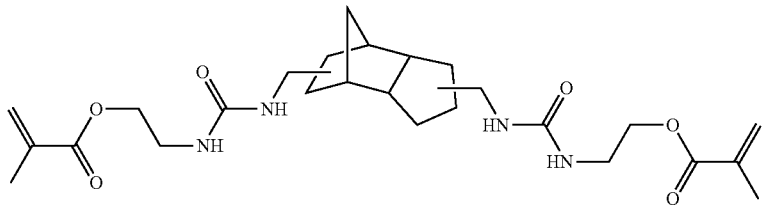

Here again, there are still active hydrogen atoms capable of reacting with nitrogen which for example with an excess of isocyanate react to form the biuret of Formula (27).

Formula (27)

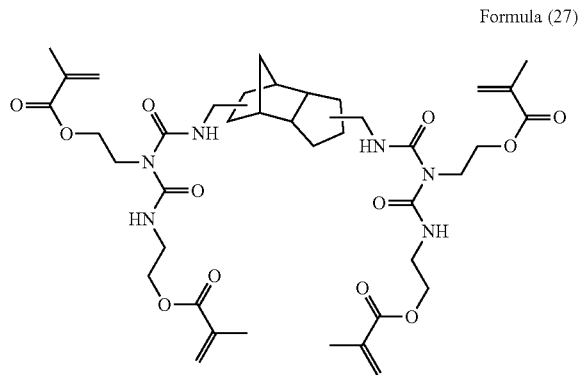

Formula (28)

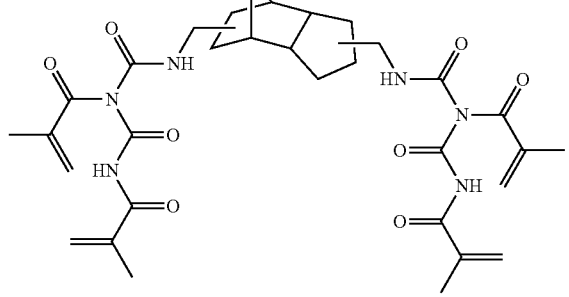

By analogy to the monomers described above, which comprise a polyalicyclic structure element Q derived from the tricyclo[5.2.1.0²,⁶]decane, monomers can also be prepared, which comprise a polyalicyclic structure element Q derived from a tricyclo[3.3.1.1$^{3,7}$]decane (adamantane). The following reaction products are shown by way of examples:
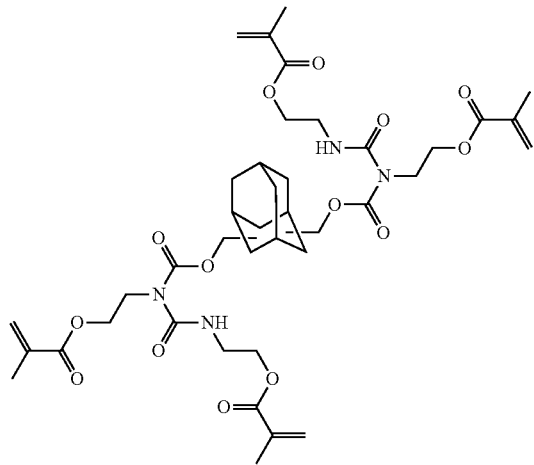
Formula (29)
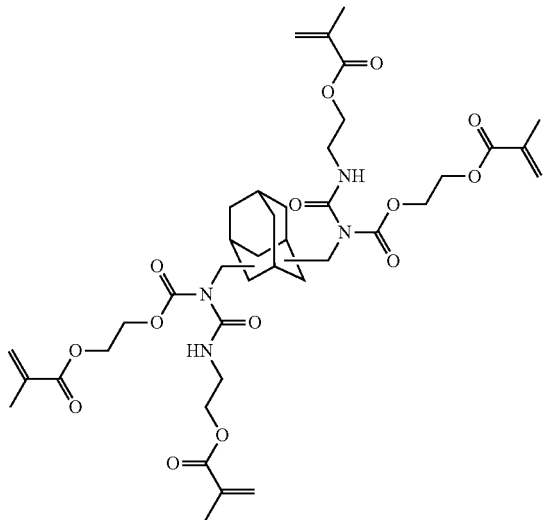
Formula (30)
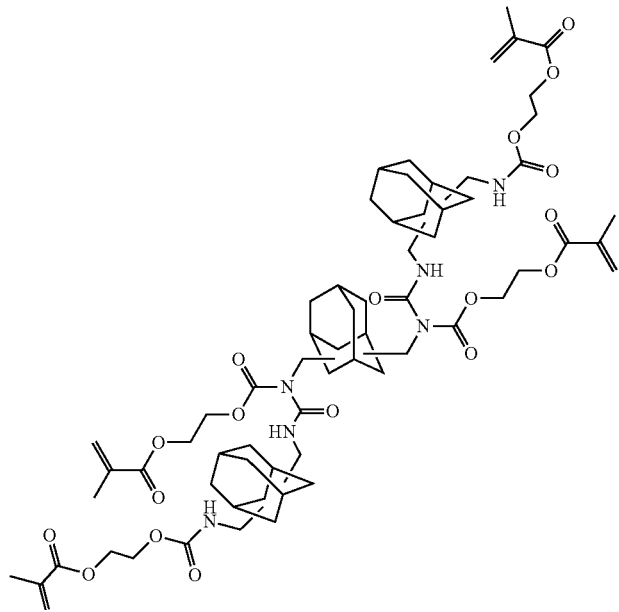
Formula (31)

Formula (32)
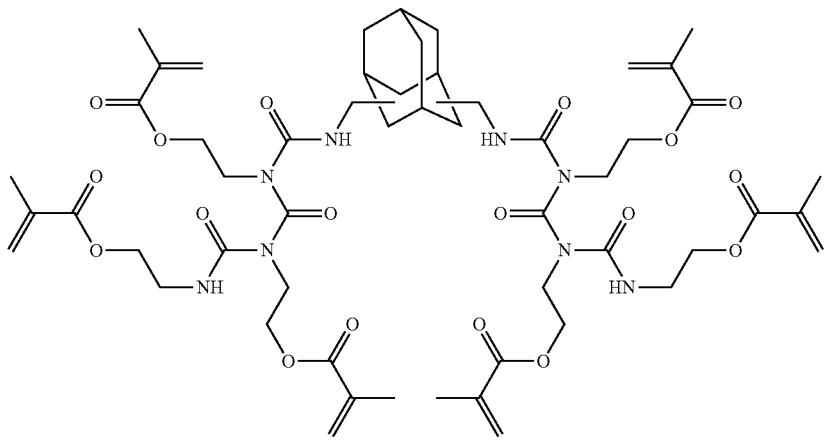
Formula (33)
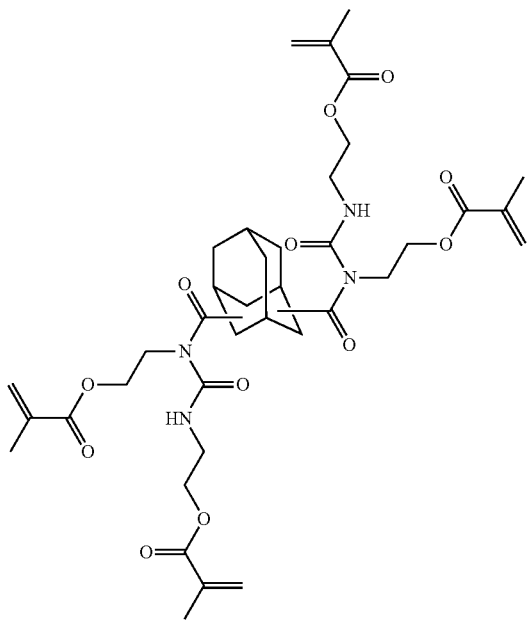
Formula (34)
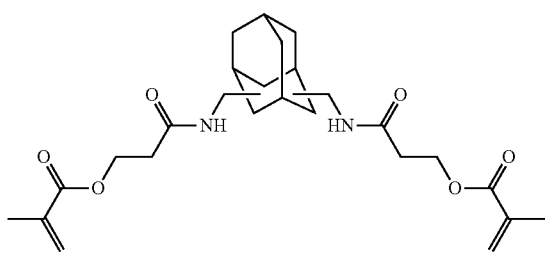
Formula (35)
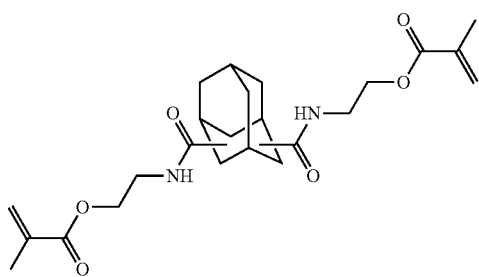

-continued
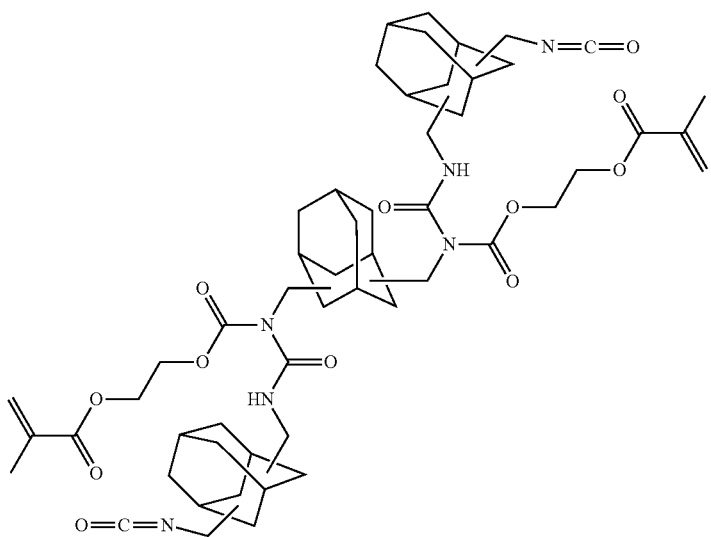
Formula (36)
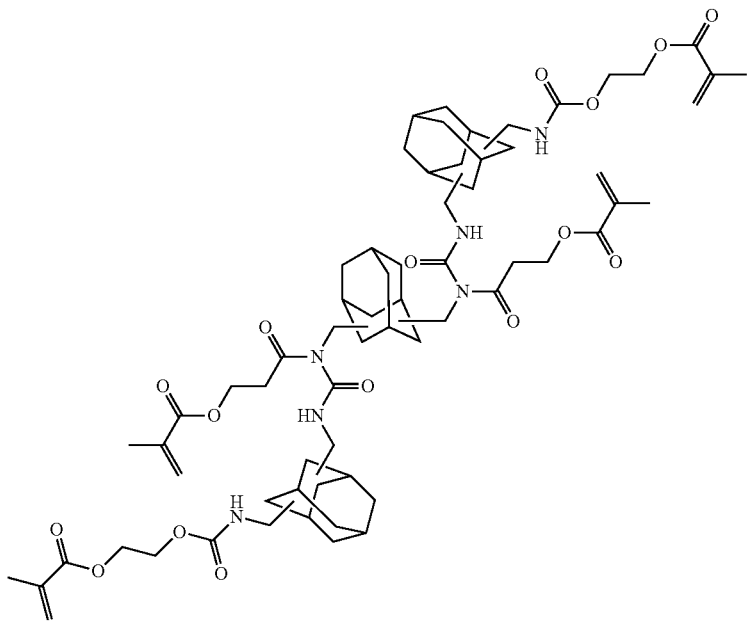
Formula (37)
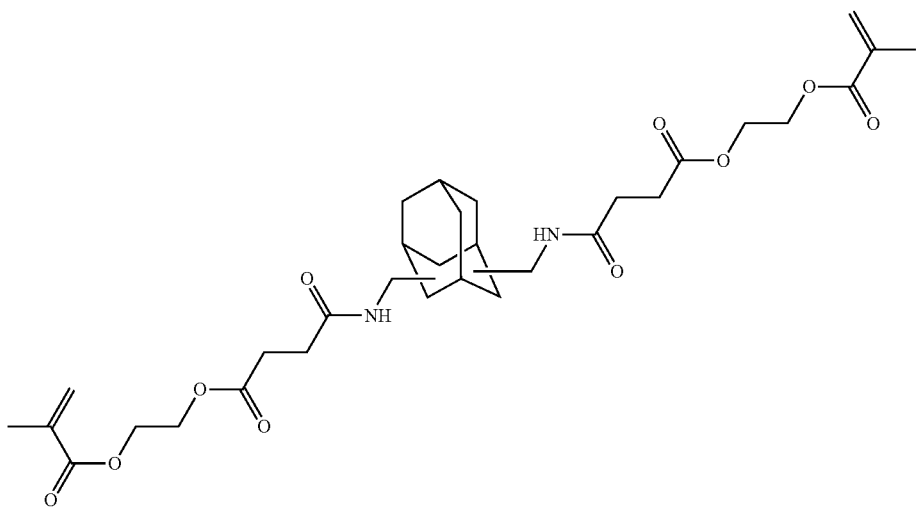
Formula (38)

-continued
Formula (39)
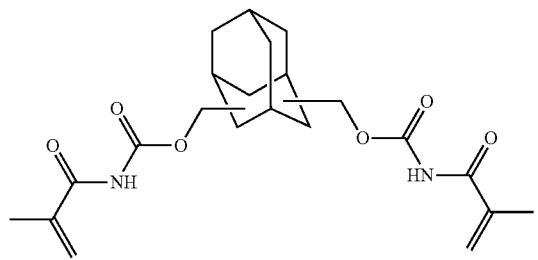
Formula (40)
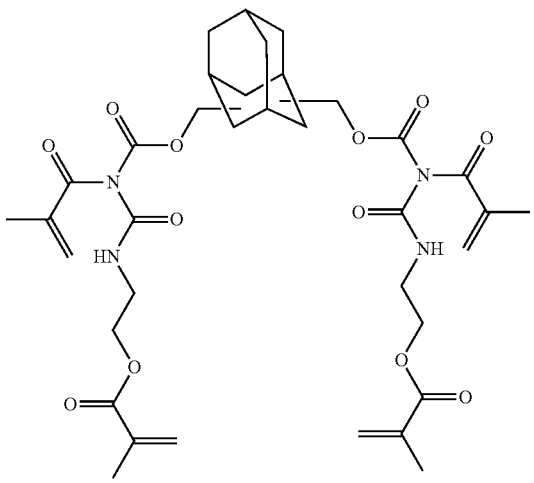
Formula (41)
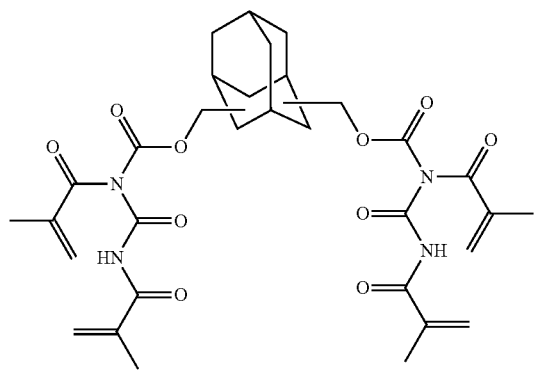
Formula (42)
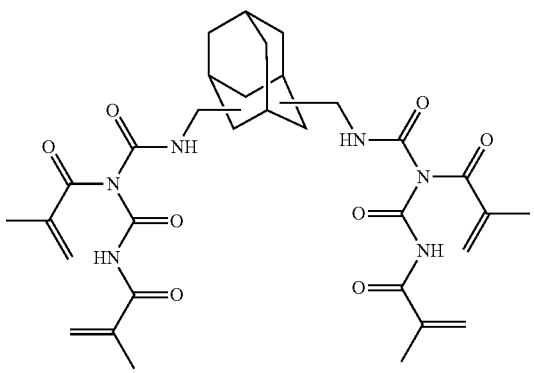
Formula (43)
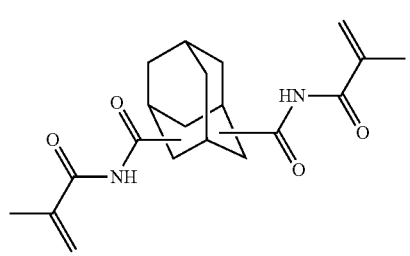

Formula (44)
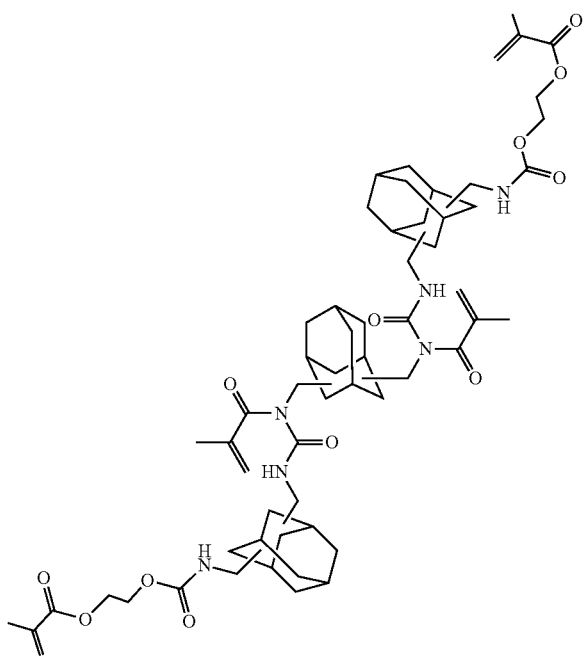
Formula (45)
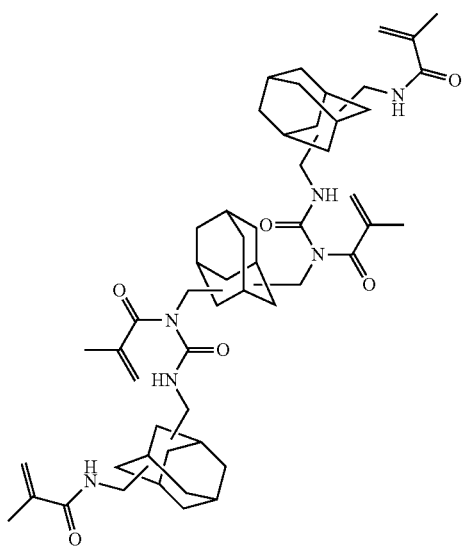
Formula (46)
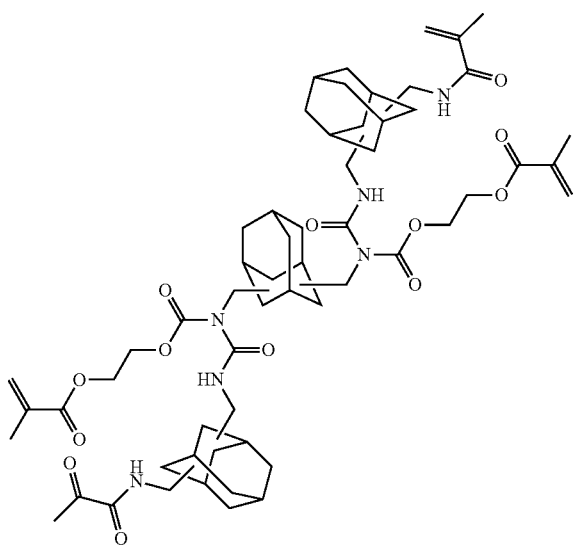

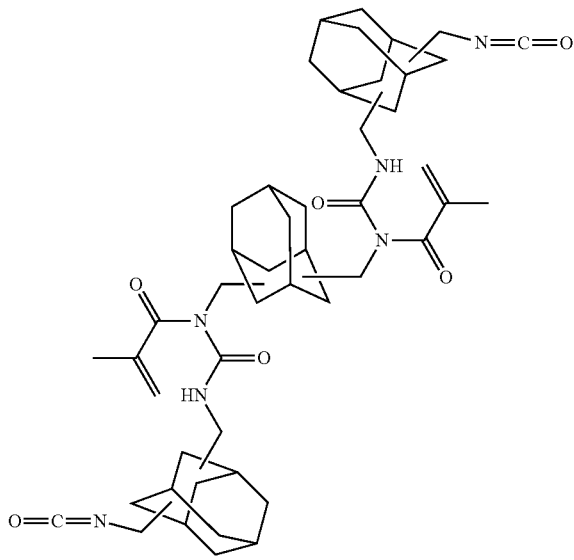

Formula (47)

In the following the invention is explained in detail for monomers comprising bicyclical structure elements Q:

A suitable starting compound is 2,5 (2,6)-bis(hydroxymethyl)bicyclo(2.2.1)heptane. 2,5 (2,6)-bis(hydroxymethyl) bicyclo(2.2.1)heptane is in itself known and available commercially or from norbornadiene (preparable from cyclopentadiene and ethine) through hydroformulation and subsequent reduction of the diformylnorbornane to norbornanediol. The hydroformulation of the norbornadiene can take place both conventionally and unconventionally.

In the conventional method norbornadiene is reacted in an organic solvent, for example toluene, in an autoclave under pressure (100 atm) and high temperatures (100° C.) in the presence of a catalyst with the synthesis gas CO/H$_2$ (1:1). After a reaction time of 90 minutes no further substrate can be detected and the reaction is completed with the formation of the dialdehydes with high selectivity. As main components the two isomers of the exo-exo-dialdehyde are formed. As catalysts [Pt(C$_2$H$_4$)(dppb)]/CH$_3$SO$_3$H are used. The abbreviation "dppb" means 1,4-bis(diphenylphosphino)butane. A detailed preparation specification can be found in the Journal of Organometallic Chemistry, 447, 153-157, 1993 in an article by C. Botteghi, S. Paganelli, A. Perosa, R. Lazzaroni, G. Uccello-Baretta entitled "Hydroformylation of norbornene and 2,5-norbornadiene catalyzed by platinum-(0)-alkene complexes in the presence of methanesulfonic acid: determination of the stereochemistry of the reaction". As catalytic metals cobalt or rhodium in the form of their hydrido carbonyl species (HM(CO)$_4$) can be used, such as for example on the basis of hydrido cobalt tetracarbonyl (HCo(CO)$_4$).

In the unconventional method, i.e. in supercritical carbon dioxide, hydrogen and carbon monoxide react during the catalytic conversion of the olefins to the aldehydes under much less drastic conditions than in the conventional method. At just 20 bar and 100° C. in the presence of Rh/4-H$^2$F$^6$-TPP the reaction takes place within 30 minutes almost quantitatively with a proportion of 95% dialdehydes. During the rhodium catalyzed hydroformulation in supercritical carbon dioxide, in order to increase the solubility of the Rh-catalyst in CO$_2$ the triphenylphospine ligand is derivatized with perfluoralkyl groups, wherein the electronic effect on the metal centre is reduced to a minimum by means of two CH$_2$ groups, so-called spacers. The acronym 4-H$^2$F$^6$-TPP thus means that position 4, therefore in para position of the aromatic ring (seen from the P atom), initially the CH$_2$ groups connect, followed by 6 CF$_2$ groups. More detailed preparation specifications can be found in the dissertation by H. Stemmer, 2001, Friedrich-Schiller-Universität Jena, entitled "Homogene Katayse in überkritischem Kohlendioxid: Analogien and Unterschiede zu konventionellen Lösungsmitteln" (*Homogenous catalysis in supercritical carbon dioxide: Analogies to and differences from conventional solvents*).

A further suitable starting compound is 2,5 (2,6)-bis(isocyanatomethyl)bicyclo[2.2.1]heptane according to the following graphic formulas:

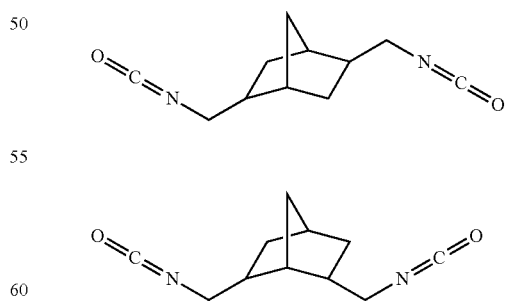

In the following a number of examples are provided of monomers comprising a bicyclic structure element Q derived from bicyclo[2.2.1]heptane.

Formula (48)
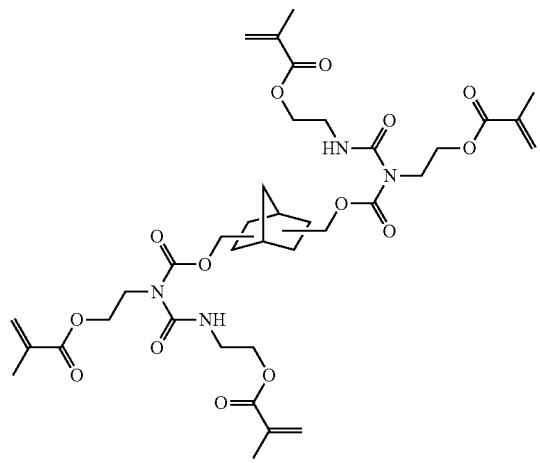
Formula (49)
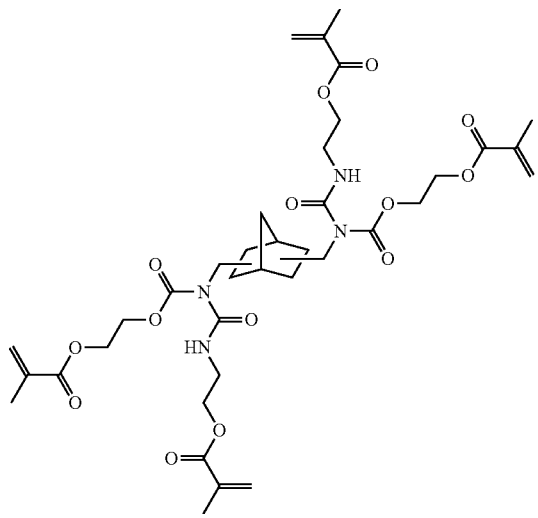
Formula (50)
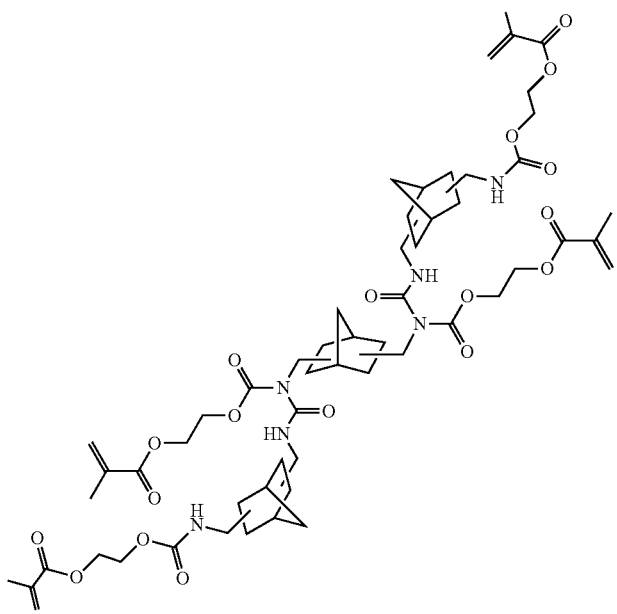
Formula (51)
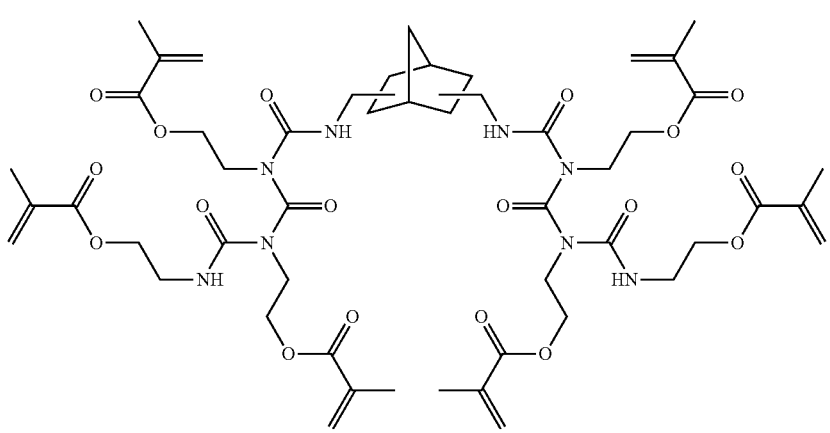

-continued
Formula (52)
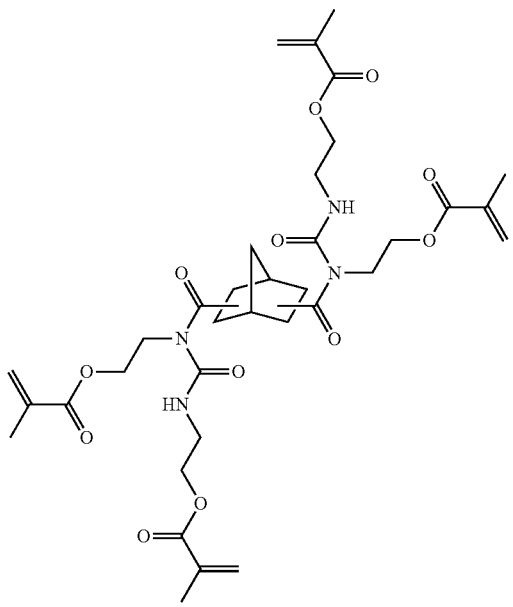
Formula (53)
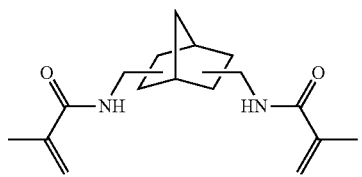
Formula (54)
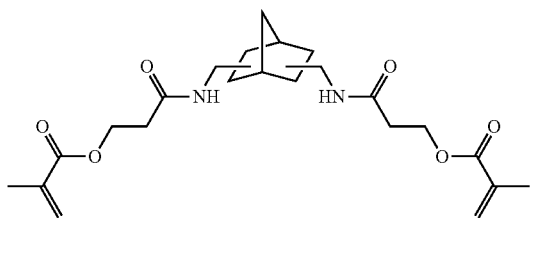
Formula (55)
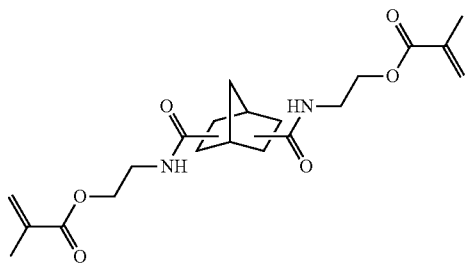
Formula (56)
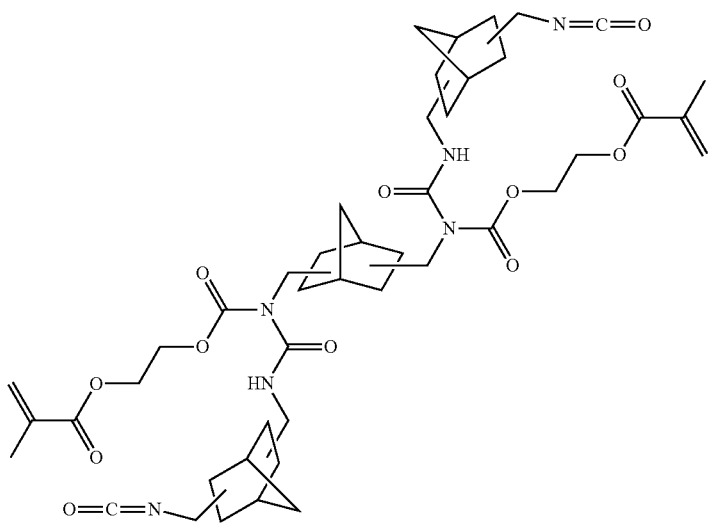

Formula (57)
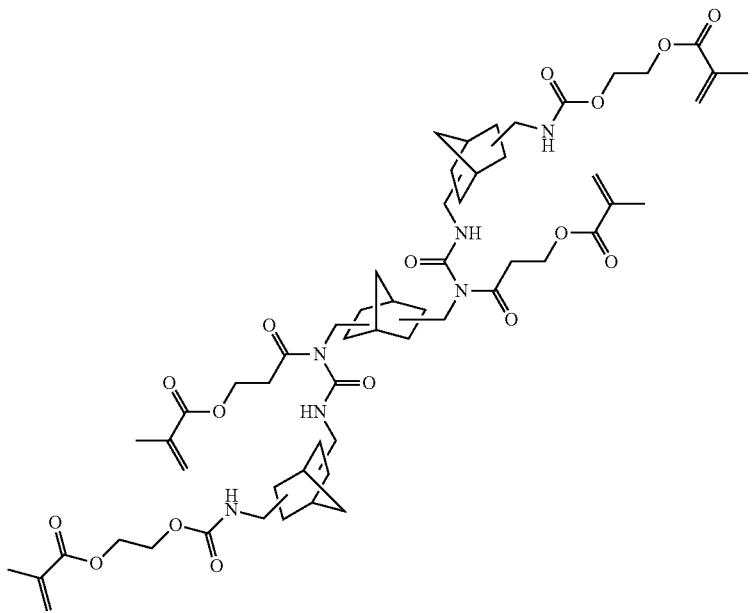
Formula (58)
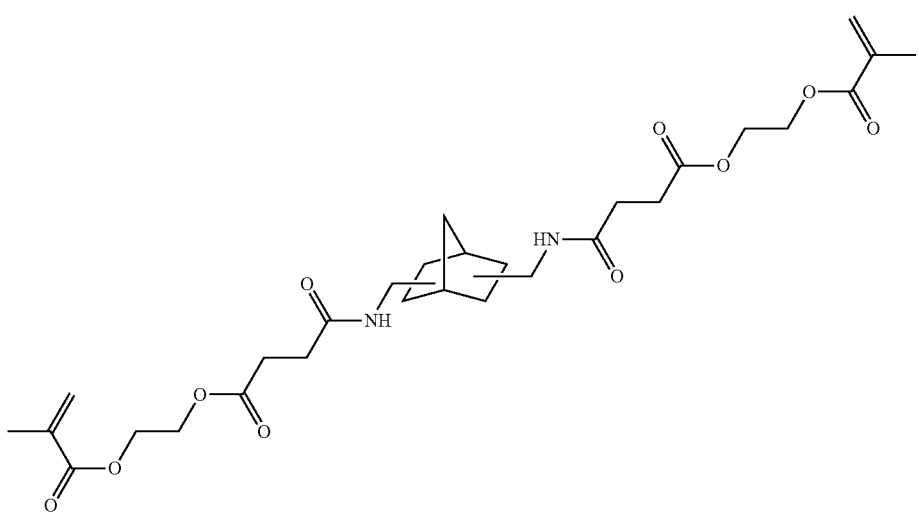

Formula (59)
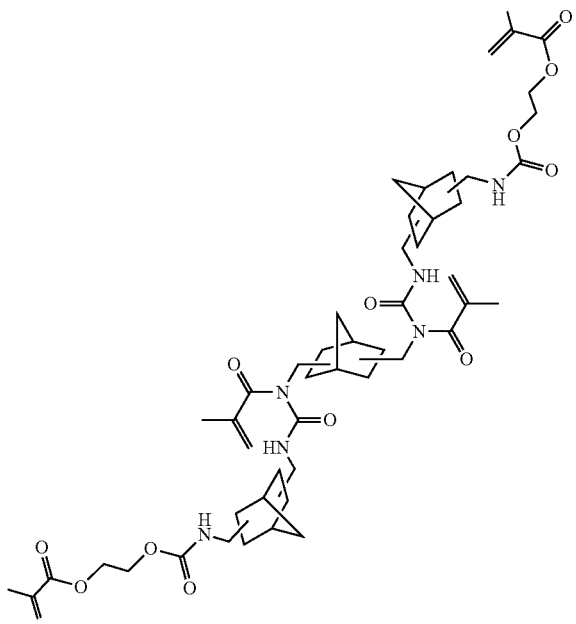
Formula (60)
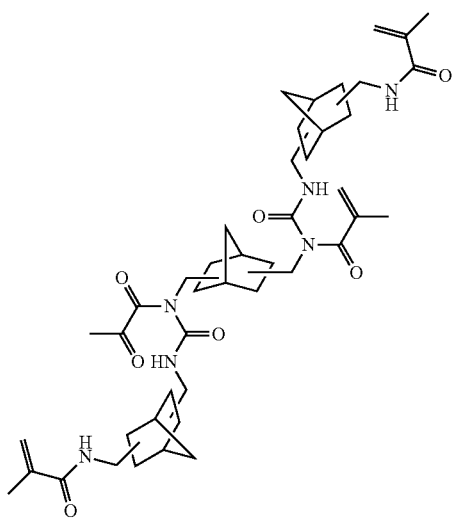
Formula (61)
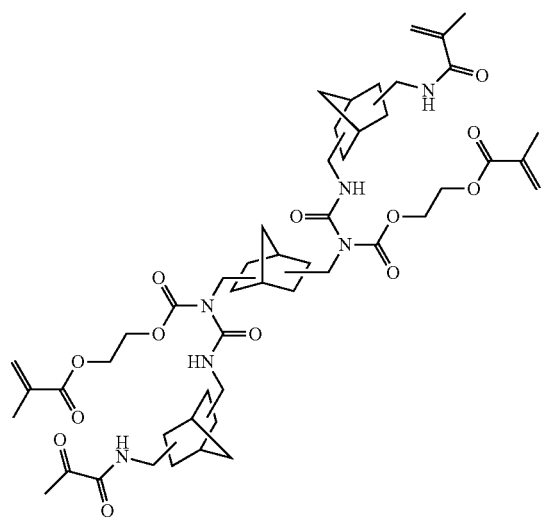
Formula (62)
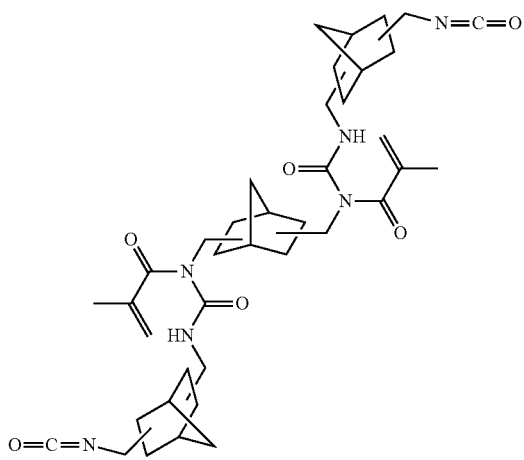
Formula (63)

Formula (64)

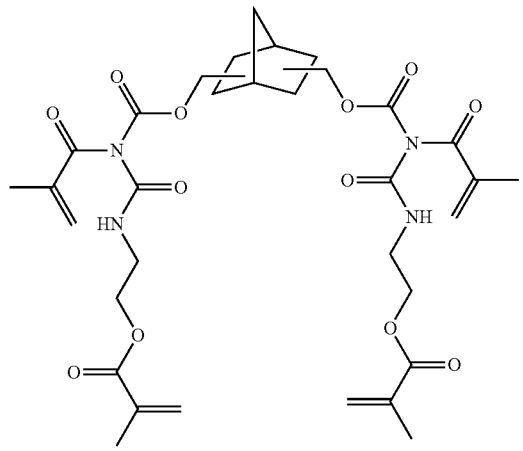

Formula (65)

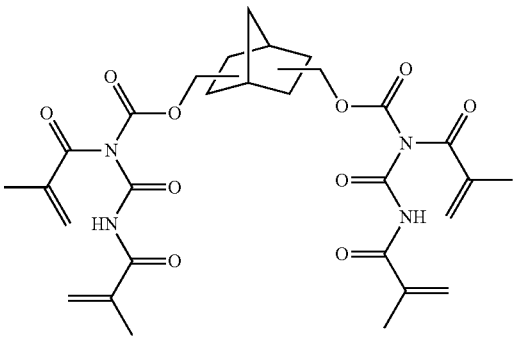

Formula (66)

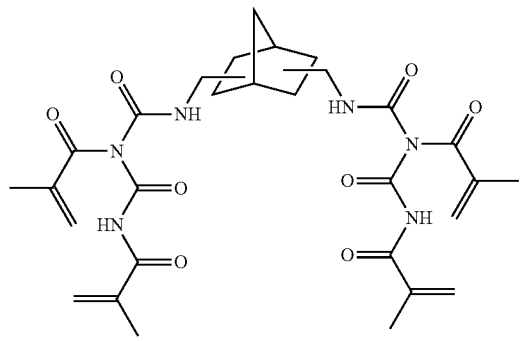

Formula (67)

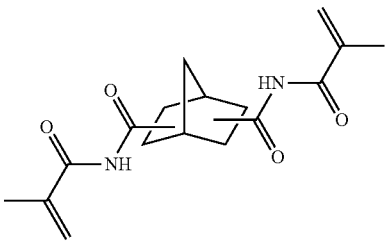

A monomer according to the invention can comprise two or a plurality of polyalicyclic structure elements, wherein these may be identical or different.

A monomer according to the invention, whose molecule comprises two polyalicyclic structure elements that differ from one another, is for example obtainable by reacting the TCD-urethane of formula (11) first with diisocyanatonorbornane [bis(isocyanatomethyl)bicyclo[2.2.1]heptane] and then with 2-hydroxyethyl methacrylate, leading to the compound of Formula (68).

Formula (68)

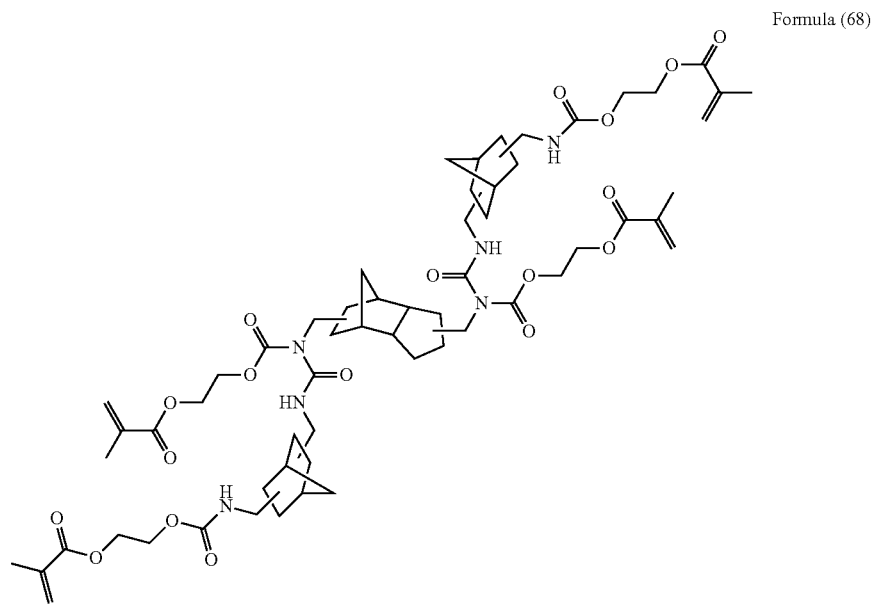

The corresponding reaction of the compound of Formula (11) with diisocyanatoadamantane [(bis(isocyanatomethyl)tricyclo[3.3.1.1$^{3,7}$]decane] likewise provides a monomer according to the invention, the molecule of which comprises two polyalicylic structure elements Q that differ from one another, as shown in the following graphic formula of the compound of Formula (69).

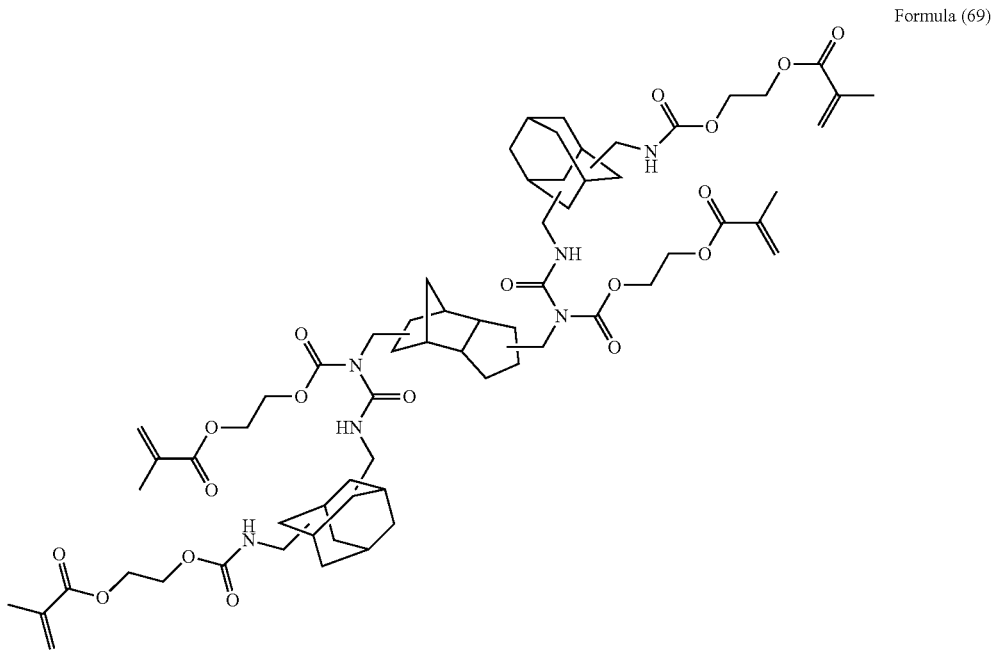

Formula (69)

The preparation of the monomers according to the invention is based on the in itself known "diisocyanate polyaddition method". With this method the isocyanate groups with for example alcoholic hydroxyl groups join together rapidly and extensively quantitatively through an addition reaction by generating heat. Here the isocyanates, apart from steric influences, react more quickly with addition partners the more nucleophilic the addend is and the more electrophillic the isocyanate.

The reaction is generally performed in an inert solvent such as THF (tetrahydrofuran), toluene, xylene, methylene chloride or acetonitrile. The reaction can also be conducted optionally without a solvent.

There are two main classes of suitable catalysts for the isocyanate addition reaction: firstly tertiary amines (such as tri-N,N-dimethylaminomethyl phenol or 1,4-diazabicyclo(2,2,2)octane, also referred to as triethylene diamine), which through abstraction of the hydroxyl hydrogen atom and formation of alcoholate aniones activate the alcohols and thus accelerate their nucleophilic attack on the isocyanate carbon atom, and secondly a series of metalorganic compounds, which as Lewis acids increase the electrophilia of the isocyanate hydrogen atom. Preference is for the use for the reactions according to the invention of metal salts of higher fatty acids such as dibutyltin laurate, tin (II) octoate, etc. or compounds such as iron (III) acetylacetonate. Highly preferred is the use of dibutyltin laurate.

The catalyst is preferably used in quantities of 0.01 through 2 wt. %, preferably 0.08 through 1 wt. %, in relation to the total quantity of reactants according to A) and B) and optionally C) and optionally D).

In a preferred embodiment the method can comprise the addition of a polymerization inhibitor. Common and suitable inhibitors are for example hydroquinone monomethylether, hydroquinone and 2,6-di-tert.-butyl-4-methyl phenol. Further suitable inhibitors are mentioned in EP 0 783 880. The addition of inhibitors generally takes place in a quantity of 0.001 through 1 wt. %, preferably 0.01 through 0.5 wt. %, in relation to the total weight of the reactants.

The method is preferably performed with the exclusion of water. For the synthesis, a surface-grinding apparatus is then preferably used, to which an agitator, a cooler with drying tube fitted, which is filled with dry diatomaceous earth, an adjustable thermometer that control the heating rate of the mushroom heater, and a dropping funnel are attached. The apparatus is heated with a Bunsen burner flame prior to being loaded with the educts.

The reaction takes place in the temperature range 0 through 160° C., preferably in the range 30 through 140° C. and particularly preferably in the range 60 through 120° C. The reaction is preferably carried out at normal pressure.

The progress of the reaction is monitored by the change in concentration of isocyanate groups. The reaction of the isocyanate groups can take place either according to the wet chemical or the spectroscopic route. The wet chemical principle for analysis of the isocyanate groups is based on the quantitative reaction of the isocyanate with an excess of dibutyl amine and back titration of the excess amine with hydrochloric acid against bromophenol blue until the blue turns to yellow. Spectroscopically, NCO groups absorb in wavelengths of 2275 through 2250 cm$^{-1}$. The band demonstrates a very high intensity in this range, the position of which is also not influenced by conjugation. The characteristic wavelength range of the NCO band is identified if a purely qualitative spectrum of the isocyanate compound in a suitable solvent, which may also be used for the further syntheses, is created. The solvent should not have any absorption bands in the wavelength range, which demonstrate the characteristic absorption bands of the NCO group. If for example toluene is used as the solvent, then the extinction maximum of the NCO band at 2267 cm$^{-1}$ can be selected as a "window", thus as the wavelength range of the characteristic absorption band.

The reaction is conducted until the isocyanate band disappears completely.

The monomers according to the invention can advantageously also be used without any special method for purification as monomer building blocks.

The monomers according to the invention can be used individually, as mixtures comprising two or a plurality of monomers according to the invention and in mixtures with one or a plurality of conventional monomers and so-called cross-linkers. By mixing two or a plurality of different monomers according to the invention or one, two or a plurality of monomers according to the invention with one, two or a plurality of conventional monomers the viscosity, for example, can be adapted to the intended purpose. Thus monomers according to the invention can for example be combined with comonomers of lower viscosity.

The monomers according to the invention can be used wherever, liquid, flowable starting materials are to be cured to form solid end products. The transition from the liquid to the solid phase is initiated here chemically, by radiation or by both (i.e. both chemically and by means of radiation). Curing is by a radical and/or ionic mechanism. Polymerization initiators that can be used are thus photoinitiators and thermal polymerization catalysts. A person skilled in the art will be acquainted with radical photoinitiators, radical thermoinitiators, cationic photoinitiators and cationic thermoinitiators and combinations of these.

Blends according to the invention comprising the monomers according to the invention can contain various additives, activators, coinitiators, solvents, fillers, stabilizers, pigments, reactive thinners, comonomers, inhibitors, molecular weight regulators, flow agents, leveling agents, antiskinning agents, defoamers, antistatics, plasticizers, lubrication agents, wetting agents and dispersing agents, preservatives such as for example fungicides and/or biocides, modifiers to adjust the rheology such as thixotropic agents and/or thickeners, sensitizers, surface-active substances, oxygen and/or radical scavengers, pigments, colorants, light stabilizers, matting agents, fire retardants, release agents, and so on, adapted to the intended use.

UV absorbers, which for example as a result of their conjugated double bonding systems and aromatic rings are capable of absorbing UV radiation, can optionally also be a constituent of a blend or product according to the invention. Examples of UV absorbers are 2-hydroxy-4-methoxybenzophenone, salicylic acid phenyl ester or 3-(2'-hydroxy-5'-methylphenyl)-benzotriazole.

The invention further relates to a product obtainable by curing a compound according to the invention, a mixture according to the invention or a blend according to the invention, preferably in each case in one of the configurations indicated above as preferred or particularly preferred.

A product according to the invention preferably relates to a polymer or a composite, preferably a dental polymer or a dental composite material.

The invention further relates to a compound according to the invention, a blend according to the invention, a mixture according to the invention or a product according to the invention, preferably in each case in one of the abovementioned preferred or particularly preferred configurations, for use as a dental material, in particular as a dental filling material, dental underfilling material, as a flowable composite material (flow material), as a fissure sealer, as a root canal filling and sealing material, as a temporary crown material, as a temporary bridge material and/or as a stump build-up material.

The invention further relates to the use of a compound according to the invention, a mixture according to the invention, a blend according to the invention or a product according to the invention for the preparation of a dental material.

The compounds, mixtures and blends according to the invention can be used in dental materials (dental compositions), in or for the preparation of adhesive, coloring, lacquering, painting and coating compositions, casting compounds, sealants, fillers, laminating resins, molding masses, binding agents and casting resins, for encapsulating electrical and electronic components, for the production of magnetic recording materials, micromechanical parts, optical switches, and glass fiber coatings, for production of three-dimensional objects by means of stereolithography, for photographic reproduction methods, for holographic recording materials, for production of printing plates, as an adhesive and for preparation of composites.

The invention therefore also relates to the use of a compound according to the invention (preferably in one of the configurations identified as preferred or particularly preferred), in a mixture (preferably in one of the configurations identified a preferred or particularly preferred) or a blend according to the invention (preferably in one of the configurations identified as preferred or particularly preferred),
  in or for the preparation of adhesive, coloring, lacquering, painting or coating compositions, sealing compounds, sealants, fillers, laminating resins, molding masses, binding agents or casting resins,
  for encapsulation of electrical or electronic components,
  for the production of magnetic recording materials, micromechanical parts, optical switches, glass fiber coatings, three-dimensional objects by means of stereolithography, printing plates or composites,
  for photographic reproduction methods or holographic recording materials,
  as an adhesive.

The invention further relates to a method for preparing a product, preferably a dental product, with the following steps:
(i) provision of a compound according to the invention, a mixture according to the invention or a blend according to the invention, in each case preferably in one of the configurations identified as preferred or particularly preferred, as a first component;
(ii) optionally preparing a preparation through mixing of the first component with one or a plurality of further components, preferably with one or a plurality of further dental materials;
(iii) curing the component(s) from step (i) or the preparation according to step (ii), wherein the curing preferably takes place chemically and/or is light induced or thermally induced.

In a preferred configuration for this purpose the first component or the preparation according to step (ii) before curing in step (ii) is applied to, introduced into and/or placed at the envisaged position, preferably a position in the oral cavity, wherein this position preferably comprises at least one or a plurality of areas of the oral cavity from the group consisting of tooth structure (one or a plurality of teeth or parts of a tooth (in particular tooth stump, enamel, dentin, pulp, tooth neck, tooth edge)), gum and/or an area below a tooth (in particular root and root canal).

The invention further relates to a compound according to the invention, a mixture according to the invention, a curable blend according to the invention or a product according to the invention as or for use as a dental filling material, a dental underfilling material, a flow material, as a fissure sealer, as a root canal filling and sealing material, as a temporary crown material, as a temporary bridge material and/or as a stump build-up material.

The invention further relates to a method for treating a dental disease, wherein one or a plurality of compounds according to the invention, a mixture according to the invention, a curable blend according to the invention or a dental product according to the invention, preferably in one of the configurations identified as preferred, is/are used as a dental filling material, a dental underfilling material, as a flow material, as a fissure sealer, as a root canal filling and sealing material, as a temporary crown material, as a temporary bridge material and/or as a stump build-up material.

The method can include providing the one or a plurality of compounds according to the invention, a mixture according to the invention, a curable blend according to the invention or a dental product according to the invention as described herein and applying at least one of the same to tissue of a patient as part of the procedure, such as a dental procedure. The method can further include curing the compound, mixture or blend. As used herein, "tissue" is intended to have its conventional meaning and include all features of teeth.

The invention further relates to the use of a compound according to the invention, preferably in one of the configurations identified as preferred or particularly preferred, in a composite material, preferably in a dental composite material.

In a preferred configuration the invention relates to a composite material comprising or consisting of:
(a) one or a plurality of compounds according to the invention or a blend according to the invention, preferably in one of the configurations identified as preferred or particularly preferred,
  (b-1) monomers differing from constituent (a), which are copolymerizable with constituent (a), preferably photopolymerizable monomers, preferably selected from the group consisting of acrylates and methacrylates,
  (b-2) 10 through 75 wt. %, in relation to the total weight of the composite material, of a filler component consisting of
    (b-2a) 10 through 60 wt. % non-agglomerated, organically surface-modified nanoparticles with an average particle size of less than 100 nm (particularly preferably less than 60 nm)
    and/or
    (b-2b) 20 through 75 wt. % of microparticles with an average particle size of 0.4 µm through 10 µm
    and
    (b-2c) 0 through 15 wt. % of further fillers, wherein the fillers are not selected from the group of fillers b-2a and b-2b,
  wherein the weight percentages given for components (b-2a), (b-2b) and (b-2c) in each case relate to the total weight of the composite material,
  (b-3) one or a plurality of initiators and/or catalysts, and optionally one or a plurality of additives.

Such a dental composite material is suitable for the sealing of fissures and of carious lesions, and for surface sealing of restorations, since it is characterized by very low water absorption, very good surface affinity to the tooth structure and exceptional mechanical properties.

The present invention therefore also relates to such as composite material according to the invention for use as a dental sealing material, in particular as a dental sealing material for the sealing of fissures, for sealing of pits, for sealing of carious lesions, for veneering damaged enamel surfaces, for repairing minor defects to synthetic and amalgam fillings, for anchoring orthodontic treatment systems and/or for sealing the surface of restorations.

In a preferred configuration the invention relates to a highly-filled composite material consisting of or comprising:
(b-2) 80 through 95 wt. %, in relation to the total weight of the highly-filled composite material, of a mixture of filler particles comprising
  (b-2a) >10, particularly preferably >12 through 30 wt. % of non-agglomerated, organically surface-modified nanoparticles with an average particle size of less than 100 nm (particularly preferably less than 60 nm) and
  (b-2b) 45 through <84 wt. %, preferably 45 through <83 wt. %, of microparticles with an average particle size of 0.4 µm through 10 µm
  and
  (b-2c) optionally further fillers, wherein the fillers are not selected from the group of fillers b-2a and b-2b,
  wherein the weight percentages given for components (b-2a) and (b-2b) relate to the total weight of the composite material,
and
3 through 20 wt. %, in relation to the total weight of the highly-filled composite material, of a mixture of monomers comprising
(a) one or a plurality of compounds according to the invention or a mixture according to the invention, preferably in one of the configurations identified as preferred or particularly preferred,
  (b-1) one, two or a plurality of further radically polymerizable monomers from the group consisting of acrylates and methacrylates, preferably from the group of methacrylates,
  wherein the ratio of the weight of component (a) to the weight of component (b-1) is preferably in the range 1:3 through 3:1,
  (b-3) one or a plurality of initiators and/or catalysts, and optionally one or a plurality of additives.

In the cured state such highly-filled composite materials are characterized not only by a low polymerization shrinkage (preferably of less than 1.7 vol. %, particularly preferably less than 1.6 vol. %, measured according to the bonded disc method (Dental Materials 2004, 20, 88-95)), but also by low abrasion (preferably less than 30 µm, determined according to the ACTA method) and a high Vickers microhardness (preferably 140 or more).

A highly-filled composite material according to the invention is suitable as a dental material, in particular as a filling, underfilling, securing and/or stump build-up material, as a temporary crown and/or bridge material, as a prosthesis and/or relining material or as a flow material.

In a preferred configuration the invention relates to a lacquer composition, preferably a transparent lacquer composition, in particular a dental lacquer composition, consisting of or comprising
38 through 96 wt. % of a monomer component comprising
(a) one or a plurality of compounds according to the invention or a mixture according to the invention, preferably in one of the configurations identified as preferred or particularly preferred,
  (b-1a) one, two or a plurality of radically polymerizable monomers selected from the group consisting of methyl methacrylate, ethyl methacrylate, propyl methacrylate, butyl methacrylate and pentyl methacylate,
  (b-1b) one, two or a plurality of further radically polymerizable monomers with three or a plurality of (meth)

acrylate groups, preferably with three to six (meth)acrylate groups, in particular dipentaerythritol pentaacrylate, and (b-1c) optionally one, two or a plurality of further radically photopolymerizable monomers from the group consisting of acrylates and methacrylates, preferably from the group of methacrylates, wherein the ratio of the weight of component (a) to the total weight of the components (b-1a), (b-1b) and (b1-c) is preferably in the range 4:1 through 1:4, (b-2) 0 through 60 wt. % of a filler component, comprising one, two or a plurality of fillers selected from the group consisting of (b-2a) 0 through 60 wt. % of non-agglomerated, preferably surface-modified, nanoparticles with an average particle size of less than 200 nm (preferably less than 100 nm, particularly preferably less than 60 nm), (b-2b) 0 through 10 wt. % of microparticles with an average particle size of 0.4 μm through 10 μm, and (b-2c) 0 through 15 wt. % of further fillers, preferably 0 through 10 wt. %, preferably 0 through 5 wt. %, more preferably 0 through 2.5 wt. % of further fillers, wherein the fillers are not selected from the group of fillers b-2a and b-2b, (b-3) one or a plurality of initiators and/or catalysts, and optionally one or a plurality of additives, wherein the weight percentages given in each case relate to the total weight of the lacquer composition.

Preferably here the total quantity of component (a) and component (b-1a) in a lacquer composition according to the invention is at least 25 wt. %, preferably 30 wt. % or more, preferably 35 wt. % or more, in each case in relation to the total weight of the lacquer composition.

These preferred transparent lacquer compositions according to the invention, are suitable as protective and gloss lacquers in dentistry. These lacquer compositions have a very low water absorption and very good mechanical characteristics (in particular flexural strength and modulus of elasticity). They are furthermore characterized by a very good adaptation, i.e. very good surface affinity to the corresponding surface, in particular the tooth structure (in particular to the tooth enamel).

In the uncured state a lacquer composition according to the invention, in particular a dental lacquer composition according to the invention, is characterized by a low contact angle to the dry tooth enamel (preferably of less than 50°, preferably less than 40°, particularly preferably less than 30°, measured with a contact angle measuring instrument from Krüss (DSA 100)). Before performing the contact angle measurement to this end a human tooth was dried with a tissue ("dry tooth enamel").

It has further become apparent that a lacquer composition according to the invention, in particular a dental lacquer composition according to the invention, in the cured state has a very low water absorption, preferably less than 50 μg/mm$^3$, preferably less than 45 μg/mm$^3$, and preferably less than 40 μg/mm$^3$, particularly preferably less than 35 μg/mm$^3$. Here the water absorption was determined analogous to ISO 4049.

The lacquer compositions according to the invention have a variety of uses on different substrates and are preferably used as cavity and surface lacquer in dentistry. The lacquer compositions according to the invention are preferably used on glass ionomer fillings, temporary crowns and bridges in composite, and on composite restorations. The adhesive "interfaces" between composite and tooth structure can be protected by lacquer compositions according to the invention.

As cavity lacquers the lacquer compositions according to the invention can be used for underfilling dental filling materials and in so doing shield the pulp from damaging monomers. As a surface lacquer the lacquer compositions according to the invention can protect the tooth enamel from external negative impacts and from the substances present in the oral cavity and on the tooth surface, and prevent the occurrence of caries.

Dental lacquer compositions according to the invention are preferably designed so that they can be used as a cavity and/or surface lacquer, as an underfilling for dental filling materials, to protect the tooth enamel, to prevent caries, to protect a restoration (in particular from premature attrition), to improve the resistance to abrasion of a dental filling material, to stabilize restored surfaces, to protect against abrasion and/or discoloration of a tooth or a restoration, to close marginal gaps and/or microcracks, to smooth restored surfaces, to provide a natural sheen to a tooth or restoration and to reduce deposits of coloring matter on a tooth or a restoration. Corresponding uses of a lacquer composition according to the invention are preferred.

Furthermore, the compounds according to the invention are eminently suited to use as a root canal filling and/or sealing material.

In a preferred configuration the invention relates to a curable dental composition for filling and sealing a root canal consisting of or comprising:

(a) 5 wt. % or more of one or a plurality of compounds according to the invention or a mixture according to the invention, preferably in one of the configurations identified as preferred or particularly preferred, (b-1) 5 wt. % or more of one, two or a plurality of further polymerizable monomers from the group consisting of acrylates and methacrylates, preferably with a polyetherpolyol structure element, here preferably one or a plurality of polyethylene glycoldi(meth)acrylates with 4 through 10 ethylene oxide units, (b-2) 35 through 80 wt. % of a filler component comprising one, two or a plurality of radiopaque fillers, and (b-3) one or a plurality of initiators and/or catalysts, and optionally further additives, wherein the total quantity of the monomers of components (a) and (b-1) is preferably 20 wt. % or more, and/or wherein the total quantity of the radiopaque fillers of component (b-2) is preferably in the range 30 through 75 wt. %, preferably in the range 40 through 70 wt. %, more preferably in the range 50 through 70 wt. %, particularly preferably in the range 55 through 65 wt. %, wherein the weight percentages given in each case relate to the total weight of the composition.

In order to achieve even better adhesion to the tooth enamel and/or dentin, the compounds according to the invention can preferably be combined with one or a plurality of adhesion-promoting additives.

Preference is therefore for blends according to the invention, which contain as component (b-6) one or a plurality of adhesion-promoting additives.

Greater preference is for blends according to the invention comprising (a) one or a plurality of compounds according to the invention or a mixture according to the invention, preferably in one of the configurations identified as preferred or particularly preferred, and (b-6) one or a plurality of adhesion-promoting additives, selected from the group consisting of polymerizable or non-polymerizable acids or carboxylic acid anhydrides, preferably from the group consisting of phosphoric acids, phosphonic acids, carboxylic acids and their salts, carboxylic acid esters and carboxylic acid anhydrides,
preferably in a quantity in the range 0.1 through 5 wt. %, more preferably in a quantity in the range 0.5 through 2.5 wt. %, in each case in relation to the total weight of the composition.

Preferably the one or a plurality of adhesion-promoting additives of component (b-6) is/are selected from the group consisting of
10-(meth)acryloyloxydecyl dihydrogen phosphate (10-MDP), 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyun-decyl dihydrogen phosphate, 20-(meth)acryloyloxyeicosyl dihydrogen phosphate, 1,3-di(meth)acyloyloxypropyl-2-dihydrogen phosphate, 2-(meth)acryloyloxyethylphenyl dihydrogen phosphate, di(2-(meth)acyloyloxyethyl)pyrophosphate, di(2-(meth)acyloyloxypropyl)pyrophosphate, di(2-(meth) acyloyloxybutyl)pyrophosphate, di(2-(meth)acyloyloxypentyl)pyrophosphate, the di(2-(meth)acyloyloxyhexyl)pyrophosphate, di(2-(meth)acyloyloxydecyl)pyrophosphate, mono-, di- and/or triesters of phosphoric acid, obtained by reaction of hydroxy-C2-C8-alkyl methacrylate (here preferably hydroxyethyl methacrylate) or glyceryl dimethacrylate with phosphoroxy chloride, glyceryl dimethacrylate phosphate, pentaerythritol trimethacrylate phosphate, dipentaerythritol-pentaacrylate phosphate, tetramethacryloxyethyl pyrophosphate, 4-(methacryloyl-oxyethyl) trimellitic acid, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate, methacryloyloxy ethyl phthalate, methacryloyloxy ethyl maleate, methacryloyloxy ethyl succinate, 1,3-glycerol dimethacrylate maleate and di-oxyethoxy methacrylic acid ethylene diamine tetraacetic acid ester.

Here in turn preferred adhesion-promoting additives of component (b-6) are 10-(meth)acryloyloxydecyl dihydrogen phosphate (10-MDP), glyceryl dimethacrylate phosphate, pentaerythritol trimethacrylate phosphate, dipentaerythritol pentaacrylate phosphate, tetramethacryloxy ethyl pyrophosphate, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate.

Similarly preferred are curable dental compositions according to the invention for filling and/or sealing a root canal (as defined above), which contain as component (b-6) one or a plurality of adhesion-promoting additives, since the adhesion to the dentin is relevant for such compositions. Here also the configurations identified as preferred or particularly preferred apply by analogy.

EXAMPLES

The invention is further explained using the following examples. Unless otherwise indicated all data relate to the weight. The following abbreviations common in the trade are used here:

BHT=2,6-di-tert.butyl-4-methyl phenol
UDMA=urethane dimethacrylate (7,7,9-trimethyl-4,13-dioxo-5,12-diazahexadecane-1,16-dioxydimethacrylate)
CQ=campherquinone
DABE=ethyl-p-N,N-dimethylaminobenzoate
Bis-GMA=bisphenol-A-glycidyl-methacrylate
TEDMA=triethylene glycol dimethacrylate For the catalyst solution used in the following 0.50 g of dibutyltin(II)dilaurate were dissolved in 9.50 g toluene.

Example 1

Synthesis of the Compound of Formula (1) (not According to the Invention)

1.90 g (9.68 mmol) of 3(4), 8(9)-bis(hydroxymethyl)tricyclo[5.2.1.0$^{2,6}$]decane were dissolved in 10 ml of tetrahydrofuran and 0.04 g of BHT and 0.105 g of the catalyst solution were added. Under agitation 3.00 g (19.34 mmol, 2 equivalents) of isocyanatoethyl methacrylate dissolved in 10 ml of THF were dropped in. Once addition was complete the dropping funnel was replaced by a reflux condenser and the reaction mixture heated to 60° C. with the continuation of the reaction being monitored by IR spectroscopy. After 24 hours no further isocyanate bands could be detected. The solvent was removed using the rotary evaporator. The urethane of formula (1) was obtained in a yield of 3.40 g (6.74 mmol, 70%) as a light yellowy oil.

Example 2

Synthesis of the Compound of Formula (2)

0.95 g (4.84 mmol) of 3(4), 8(9)-bis(hydroxymethyl)tricyclo[5.2.1.0$^{2,6}$]decane were dissolved in 10 ml of toluene and 0.04 g of BHT and 0.103 g of the catalyst solution were added. Under agitation 3.00 g (19.34 mmol, 4 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 72 hours a further 0.102 g of catalyst solution was added and heating continued until no further isocyanate bands were detected. The solvent was removed using the rotary evaporator. The allophanate of formula (2) was obtained in a yield of 3.83 g (4.69 mmol, 97%) as a light yellowy oil.

Example 3

Synthesis of the Compound of Formula (26) (not According to the Invention)

1.88 g (9.67 mmol) of 3(4), 8(9)-bis(aminomethyl)tricyclo[5.2.1.0$^{2,6}$]decane were dissolved in 10 ml of tetrahydrofuran and 0.04 g of BHT and 0.104 g of the catalyst solution were added. Under agitation 3.00 g (19.34 mmol, 2 equivalents) of isocyanatoethyl methacrylate dissolved in 10 ml of THF were dropped in. Once addition was complete the dropping funnel was replaced by a reflux condenser and the reaction mixture heated to 60° C. with the continuation of the reaction being monitored by IR spectroscopy. After 3 hours no further isocyanate bands could be detected. The solvent was removed using the rotary evaporator. The compound of formula (26) was obtained in a yield of 3.90 g (7.76 mmol, 80%) as a light yellowy oil.

Example 4

Synthesis of the Compound of Formula (27)

0.94 g (4.84 mmol) of 3(4), 8(9)-bis(aminomethyl)tricyclo[5.2.1.0$^{2,6}$]decane were dissolved in 10 ml of toluene and 0.04 g of BHT and 0.104 g of the catalyst solution were added. Under agitation 3.00 g (19.34 mmol, 4 equivalents) of isocyanatoethyl methacrylate dissolved in 10 ml of toluene were dropped in. Once addition was complete the dropping funnel was replaced by a reflux condenser and the reaction mixture heated to 100° C. with the continuation of the reaction being monitored by IR spectroscopy. After 2 days no further isocyanate bands could be detected. The solvent was removed using the rotary evaporator. The biuret of formula (27) was obtained in a yield of 3.90 g (4.79 mmol, 99%) as a light yellowy oil.

Example 5

Synthesis of Compound AX1

1.19 g (6.46 mmol) of 1,3,5-trihydroxyadamantane were dissolved in 10 ml of tetrahydrofuran and 0.04 g BHT and 0.105 g of the catalyst solution were added. Under agitation 3.00 g (19.34 mmol, 3 equivalents) of isocyanatoethyl methacrylate dissolved in 10 ml of THF were dropped in. Once addition was complete the dropping funnel was replaced by a reflux condenser and the reaction mixture heated to 60° C. with the continuation of the reaction being monitored by IR spectroscopy. After 6 days no further isocyanate bands could be detected. The solvent was removed using the rotary evaporator. Compound AX1 was obtained in a yield of 3.61 g (5.69 mmol, 88%) as a crystalline solid.

Example 6

Synthesis of Compound AX2

0.60 g (3.26 mmol) of 1,3,5-trihydroxyadamantane were dissolved in 20 ml of toluene and 0.04 g BHT and 0.101 g of the catalyst solution were added. Under agitation 3.03 g (19.54 mmol, 3 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 6 days no further isocyanate bands could be detected. The solvent was removed using the rotary evaporator. The allophanate AX2 was obtained in a yield of 3.52 g (3.16 mmol, 97%) as a white solid.

Example 7

Synthesis of the Compound of Formula (35)

0.59 g (3.07 mmol) of 1,3-dicarboxyadamantane were dissolved in 20 ml of toluene and 0.04 g BHT and 0.105 g of the catalyst solution were added. Under agitation 0.93 g (5.99 mmol, 2 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 2 days no further isocyanate bands could be detected. The solvent was removed using the rotary evaporator. The acyl urea AX3 was obtained in a yield of 1.34 g (3.00 mmol, 98%) as a white solid.

Example 8

Synthesis of a Mixture According to the Invention (NCO:OH=1.25:1.00)

1.50 g (7.64 mmol) of 3(4), 8(9)-bis(hydroxymethyl)tricyclo[5.2.1.0$^{2,6}$]decane were dissolved in 10 ml of toluene and 0.04 g of BHT and 0.101 g of the catalyst solution were added. Under agitation 2.94 g (19.10 mmol, 2.5 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 4 days no further isocyanate bands were detected. The solvent was removed using the rotary evaporator. The product was obtained in a yield of 4.42 g as a light yellowy oil.

Example 9

Measurement of Strength and Water Absorption

In order to demonstrate the positive effect of the chemical structure of the monomers according to the invention on the strength and water absorption, test specimens from various example resin mixtures were prepared and their water absorption and flexural strength measured. The compositions of the resin mixtures (in wt. %) and the results of the measurements are listed in the table below.

|  | Comparative example A | Comparative example B | Comparative example C | D* | Comparative example E | F* | G* | H* | I* | J* |
| --- | --- | --- | --- | --- | --- | --- | --- | --- | --- | --- |
| UDMA | 59.55 | 59.55 | 59.55 | 59.55 | 59.55 | 59.55 | 59.55 | 59.55 | 59.55 | 59.55 |
| TEDMA | 19.85 | 39.85 | 19.85 | 19.85 | 19.85 | 19.85 | 19.85 | 19.85 | 19.85 | 19.85 |
| Monomer according to the invention* | 0 | 0 | 0 | 20.00 | 0 | 20.00 | 20.00 | 20.00 | 20.00 | 20.00 |
| Monomer of Formula (1)* | 0 | 0 | 20.00 | 0 | 0 | 0 | 0 | 0 | 0 | 0 |
| Monomer of Formula (26)* | 0 | 0 | 0 | 0 | 20.00 | 0 | 0 | 0 | 0 | 0 |
| Bis-GMA | 20.00 | 0 | 0 | 0 | 0 | 0 | 0 | 0 | 0 | 0 |
| CQ | 0.24 | 0.24 | 0.24 | 0.24 | 0.24 | 0.24 | 0.24 | 0.24 | 0.24 | 0.24 |

-continued

|  | Comparative example A | Comparative example B | Comparative example C | D* | Comparative example E | F* | G* | H* | I* | J* |
|---|---|---|---|---|---|---|---|---|---|---|
| DABE | 0.36 | 0.36 | 0.36 | 0.36 | 0.36 | 0.36 | 0.36 | 0.36 | 0.36 | 0.36 |
| Flexural strength [MPa] | 92.9 | 85.7 | 86.5 | 102.9 | 100.9 | 109.1 | 101.3 | 110.5 | 99.8 | 96.8 |
| Water absorption [µg/mm³] | 29.08 | 36.41 | 26.15 | 18.17 | 32.54 | 21.38 | 24.15 | 20.17 | 22.72 | 23.0 |

*The following monomers were used in each case:
Comparative example C: Compound of Formula (1)
Example D: Compound of Formula (2)
Comparative example E: Compound of Formula (26)
Example F: Compound of Formula (27)
Example G: Compound AX1
Example H: Compound AX2
Example I: Compound of Formula (35)
Example J: Mixture of monomers from example 8

The determination of the flexural strength took place in accordance with ISO 4049. In a PTFE mold test specimens were prepared with dimensions of 2×2×50 mm. These were then polymerized for 60 minutes in a light box. After removal from the mold the test specimens were stored for 24 hours at 37° C. in distilled water before being measured. The measurement of the flexural strength took place using a universal testing machine at a traverse speed of 0.75 mm/min and a clamping length of 25 mm until rupture.

For the water absorption likewise test specimens with a size of 2×2×50 mm³ were prepared as described above and polymerized in the light box for 60 minutes. Then the weight and the exact dimensions of the test specimens were determined to an accuracy of 0.01 mm and from these the volume calculated. The test specimens prepared in this way were stored for 72 hours at 37° C. in distilled water. After the surfaces had been dried with a tissue, the weight was determined again. By dividing the gain in weight by the volume of the test specimen the water absorption in µg/mm³ can be calculated.

A comparison of the results shows that resin mixtures comprising the monomers according to the invention for at least one of the characteristics of flexural strength and water absorption demonstrate more favorable values than the resin mixtures according to the state of the art. In most examples the resin mixtures comprising monomers according to the invention are in fact superior to the prior art in respect of both parameters.

Further Examples of Mixtures According to the Invention and Products Obtained from These by Curing:

Example D1

Dental Lacquer Composition

The following example according to the invention demonstrates a dental lacquer composition.

| Dental lacquer composition | Parts by weight |
|---|---|
| Phosphine oxide initiator | 1.998 |
| UV stabilizer | 0.029 |
| BHT | 0.017 |
| Methyl methacrylate | 9.52 |
| Dipentaerythritol pentaacrylate | 9.52 |
| Monomer of Formula (2) | 19.05 |

| Dental lacquer composition | Parts by weight |
|---|---|
| Nano-SiO₂ (average particle size 50 nm) | 59.87 |
| Flexural strength [MPa] | 112 |
| Modulus of elasticity [MPa] | 3735 |
| Contact angle [°] dry tooth enamel | 25.6 |
| Water absorption [µg/mm³] | 32.17 |

Example D2

Dental Composite Material

The following example according to the invention demonstrates a dental composite material. This composite material us suitable as a dental sealing material, in particular for the sealing of fissures, pits and carious lesions, and for repairing minor defects in synthetic and amalgam fillings or for surface sealing of restorations.

| Dental composite material | Parts by weight |
|---|---|
| Monomer of Formula (2) | 21.38 |
| UDMA | 17.35 |
| TEDMA | 12.44 |
| UV stabilizer | 0.25 |
| DABE | 0.22 |
| Catalyst (CQ) | 0.15 |
| BHT | 0.09 |
| Glass ceramic 0.7 µm (silanized) | 26.85 |
| Reactive aluminum silicate glass (<10 µm) | 4.13 |
| Aerosil | 1.65 |
| Titanium dioxide (silanized) | 0.62 |
| Nanofiller (silanized) | 14.87 |
| Flexural strength [MPa] | 138 |
| Modulus of elasticity [MPa] | 6319 |
| Contact angle [°] dry tooth enamel | 29.5 |
| Water absorption [µg/mm³] | 11.91 |
| ACTA abrasion | 75 µm |

Example D3

Highly-Filled Dental Composite Material

The following example according to the invention demonstrates a highly-filled composite material. This composite material is suitable as a filling, underfilling, securing and/or stump build-up material, as a temporary crown and/or bridge material, as a prosthesis and/or relining material or as a flow material.

| Highly-filled composite material | Parts by weight |
|---|---|
| (a) Fillers | |
| (a1) SiO$_2$-nanopartiles ($d_{50}$ = 50 nm, silanized) | 22.62 |
| (a2) Microparticles, first fraction ($d_{50}$ = 1.5 µm, silanized dental glass) | 52.44 |
| (a2) Microparticles, second fraction ($d_{50}$ = 0.7 µm, silanized dental glass) | 14.86 |
| (b) Monomers | |
| (b1) Compound of Formula (2) | 7.60 |
| (b2) UDMA | 1.90 |
| (b2) TEDMA | 0.43 |
| (c) CQ | 0.05 |
| (c) DABE | 0.075 |
| (d) BHT | 0.014 |
| (d) UV-absorber | 0.071 |
| Vickers microhardness [MHV] | 162.5 |
| ACTA [µm] | 22.6 |
| Polymerization shrinkage [%] | 1.49 |
| Quotient (MHV/(ACTA*Polymerization shrinkage)) [100/µm] | 4.83 |

Example D4

Root Canal Filling and Sealing Material

The following example according to the invention demonstrates a dual-curing dental composition, suitable for filling and/or sealing of root canals.

The following designations or abbreviations are used here:
PEG400DMA=polyethylene glycol-400-dimethacrylate
Nano-SiO$_2$=silanized SiO$_2$ particles (40 nm)
GK=highly radiopaque, Zr-containing glass ($d_{50}$=5 µm; BET surface: 0.5 m$^2$/g)
Silanized silica=silica with an average particle size of 13 nm (BET surface: 160 m$^2$/g±25 m$^2$/g)

The two respective pastes A and B had good flow and were easily miscible with one another.

Pastes A and B of the root canal sealing material

| | Paste A Parts by weight | Paste B Parts by weight |
|---|---|---|
| Nano-SiO$_2$ | 6.16 | 6.16 |
| Compound of Formula (2) | 12.30 | 12.32 |
| PEG400DMA | 12.30 | 12.32 |
| GK | 64.57 | 64.69 |
| Silanized silica | 4.11 | 4.11 |
| Allyl thiourea | 0.28 | 0.00 |
| CQ | 0.05 | 0.00 |
| DABE | 0.07 | 0.00 |
| Gamma-terpinene | 0.16 | 0.00 |
| Cumolhydroperoxide (88%) in cumol | 0.00 | 0.40 |

The two pastes A and B were mixed together in the same parts by volume (1:1 (v/v)).

The results of the measurements for the respective root canal sealing materials are listed in the table below.

| | |
|---|---|
| Flexural strength [MPa] | 7.1 |
| Modulus of elasticity [MPa] | 105 |
| Water absorption [µg/mm$^3$] | 14 |
| Water absorption | 0.57% |
| Solubility [µg/mm$^3$] | 2 |
| Solubility | 0.07% |
| Flow (ISO 6876) | 29 mm |
| Radiopacity (Al) | 6.35 mm |
| Setting time | 22 min |
| Processing time | 43 min |

The invention claimed is:

1. A compound of structure Q(YZ$_e$)$_b$, wherein here and below the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or more of the hydrogen atoms of this polyalicyclic structure element Q not substituted by substituents YZ$_e$ is or are substituted by alkyl groups, alkoxy groups, halogen atoms or trifluormethyl groups;

b is an integer selected from the group of integers 2, 3, 4;

each Z comprises a structure element, which independently of any further structure elements that form Z, selected from the group consisting of

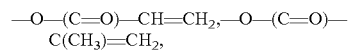

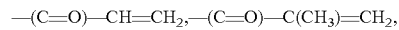

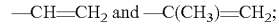

each index e is an integer, which independently of any further indices e is selected from the group of integers 1, 2, 3 and 4;

each Y represents a structure element that in the structure Q(YZ$_e$)$_b$ links the polyalicyclic structure element Q with e structure elements Z, and Y comprises a structure element selected from the group consisting of

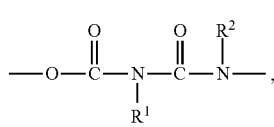

I.

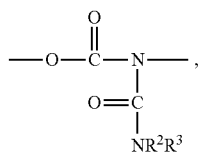

II.

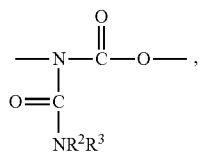

III.

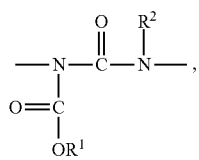

IV.

-continued $$\underset{R^1}{\overset{R^1}{\underset{|}{N}}}-\underset{}{\overset{O}{\underset{\|}{C}}}-\underset{R^1}{\overset{}{\underset{|}{N}}}-\underset{}{\overset{O}{\underset{\|}{C}}}-\underset{}{\overset{R^3}{\underset{|}{N}}}-,\quad \text{V.}$$

$$\underset{R^1}{\overset{R^1}{\underset{|}{N}}}-\underset{\underset{NR^2R^3}{\overset{O=C}{|}}}{\overset{O}{\underset{\|}{C}}}-\text{N}-,\quad \text{VI.}$$

$$-\underset{\underset{NR^2R^3}{\overset{O=C}{|}}}{\overset{O}{\underset{\|}{N}}}-\underset{}{\overset{R^1}{\underset{|}{C}}}-\text{N}-,\quad \text{VII.}$$

$$-\underset{}{\overset{O}{\underset{\|}{C}}}-\underset{R^1}{\overset{}{\underset{|}{N}}}-\underset{}{\overset{O}{\underset{\|}{C}}}-\underset{R^2}{\overset{}{\underset{|}{N}}}-,\quad \text{VIII.}$$

$$-\underset{\underset{NR^2R^3}{\overset{O=C}{|}}}{\overset{O}{\underset{\|}{C}}}-\text{N}-,\quad \text{IX.}$$

$$-\underset{\underset{R^1}{\overset{O=C}{|}}}{\overset{}{\underset{|}{N}}}-\underset{}{\overset{O}{\underset{\|}{C}}}-\underset{}{\overset{R^1}{\underset{|}{N}}}-,\text{ and}\quad \text{X.}$$

$$-\underset{\underset{NR^2R^3}{\overset{O=C}{|}}}{\overset{}{\underset{|}{N}}}-\underset{}{\overset{O}{\underset{\|}{C}}}-,\quad \text{XI.}$$

wherein $R^1$, $R^2$, and $R^3$ are independently selected from the group consisting of hydrogen, linear, branched, or ring-comprising moieties with 1 to 30 carbon atoms and 0 to 10 heteroatoms, wherein in each case the bond arranged to the left of the graphic formula is closer to the structure element Q and the bond arranged on the right is closer to the structure element Z.

2. The compound according to claim 1, wherein the compound is preparable by reacting a first reaction product, which is the reaction product of a first reaction of A) a compound of structure $QG_b$, in which each G represents a reactive group, which independently of further groups G is selected from the group consisting of ($-CH_2)_n-NH_2$, $(-CH_2)_n-(OCH_2-CHR)_m-OH$, $(-CH_2)_n-NCO$ and $(-CH_2)_n-COOH$ with B) two or more identical or different compounds $MZ_e$, wherein M represents a structure element which in each case has one or more of grouping(s) that react with the groups G selected from the group consisting of $-NH$, $-NH_2$, $-OH$, $-NCO$ and $-COOH$, wherein the following applies:

R in each case independently of any further R represents a hydrogen atom or an alkyl radical;

m is an integer selected from the group of integers from 0 through 10, each index n is an integer, which independently of any further indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the second reaction.

3. The compound according to claim 2, wherein the compound is a second reaction product from a reaction of the above first reaction product with C) a further compound according to A) or B), wherein each further compound according to A) or B) has the same meaning as in the first reaction, and/or wherein the compound is a third reaction product from a reaction of the above second reaction product with D) a further compound according to A) or B), wherein each further compound according to A) or B) has the same meaning as in the first and/or the second reaction, preferably as in the first and the second reaction.

4. The compound as claimed in claim 1, wherein Q represents a polyalicyclic structure element selected from the group consisting of bicyclic and tricyclic hydrocarbon radicals.

5. The compound as claimed in claim 4, wherein the polyalicyclic structure element is a saturated polyalicyclic structure element.

6. The compound as claimed in claim 1, wherein at least one structure element $YZ_e$ is selected independently of the other structure element(s) $YZ_e$.

7. The compound as claims in claim 6, wherein all structure elements $YZ_e$ are selected from the group consisting of $YZ_e$-A1

$$-(CH_2)_n-(OCH_2-\underset{R}{\overset{}{\underset{|}{C}H}})_m-O-\underset{}{\overset{O}{\underset{\|}{C}}}-\underset{[A]_k-Z}{\overset{R'}{\underset{|}{N}}}-(A)_k-Z,$$

$YZ_e$-A2

$$-(CH_2)_n-\underset{}{\overset{R'}{\underset{|}{N}}}-\underset{\underset{[A]_k-Z}{\|}}{\overset{O}{\underset{\|}{C}}}-\underset{}{\overset{R'}{\underset{|}{N}}}+A\underset{}{\underset{|}{]}_k}-Z,$$

-continued

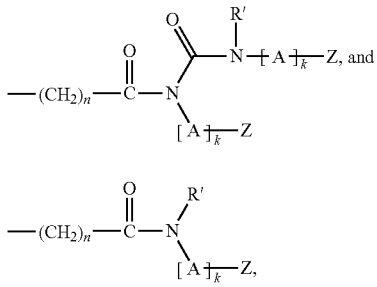

YZ_e-A3

YZ_e-A4 wherein Z, R, m and n have the meaning given above and wherein the following also applies:

each A is independently selected from the group consisting of linear, branched, or ring-comprising divalent organic bridge members with 1 to 25 carbon atoms and 0 to 10 heteroatoms, each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above, and wherein, when YZ$_e$ comprises YZ$_e$-A4, if A does not constitute a part of one of structure elements I to XI of YZ$_e$-A4, then R' is a structure element (C=O)—NH-(A)$_k$-Z.

8. The compound as claimed in claim 7, wherein each structure element A independently of any further structure elements A is selected from the group consisting of linear, branched or ring-comprising structure elements with 1 through 25 C atoms and 0 through 10 heteroatoms, wherein the heteroatoms that are optionally present are preferably selected from the group consisting of N and O.

9. The compound as claimed in claim 1, wherein all structure elements YZ$_e$ are selected from the group consisting of

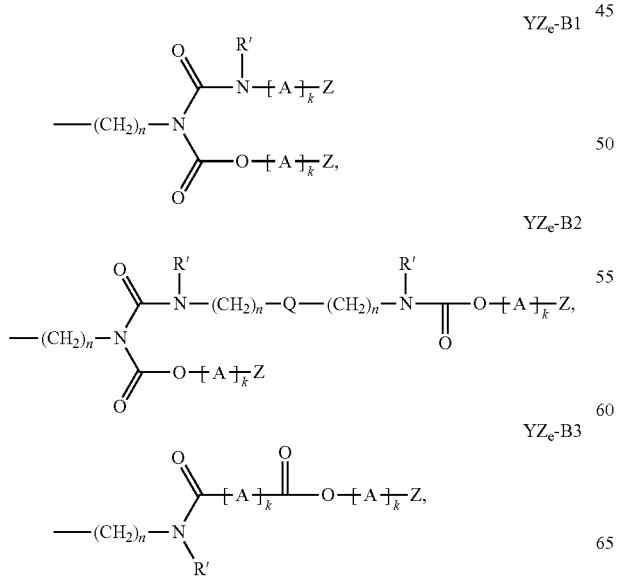

YZ_e-B1

YZ_e-B2

YZ_e-B3

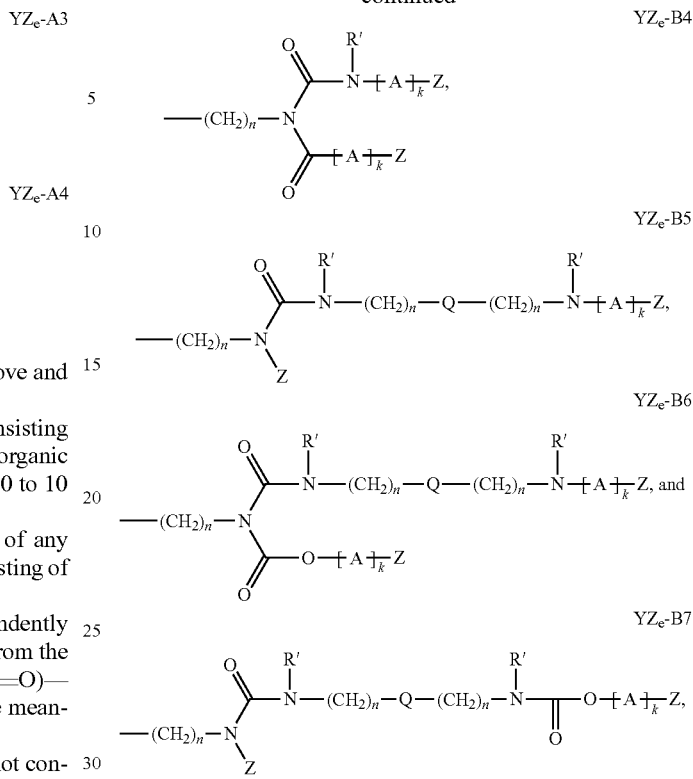

YZ_e-B4

YZ_e-B5

YZ_e-B6

YZ_e-B7 wherein each Q independently of any further structure elements Q has the above meaning, and wherein Z and n have the abovementioned meaning and wherein the following also applies:

each A is independently selected from the group consisting of linear, branched, or ring-comprising divalent organic bridge members with 1 to 25 carbon atoms and 0 to 10 heteroatoms, each index k is an integer, which independently of any further indices k is selected from the group consisting of 0 and 1;

each R' and R$^{2'}$ each represent a structure element which independently of any further structure elements R' and R$^{2'}$ is selected from the group consisting of H and a structure element (C=O)—NH-(A)$_k$-Z, wherein A, Z and k in turn have the above meanings, wherein, when YZ$_e$ comprises YZ$_e$—B3, if A does not constitute a part of one of structure elements I to XI of YZ$_e$—B3, then R' of YZ$_e$—B3 is a structure element (C=O)—NH-(A)$_k$-Z, wherein, when YZ$_e$ comprises YZ$_e$—B5, if A does not constitute a part of one of structure elements I to XI of YZ$_e$B5, then R$^{2'}$ of YZ$_e$B5 is a structure element (C=O)—NH-(A)$_k$-Z, and wherein, when YZ$_e$ comprises YZ$_e$—B7, if A does not constitute a part of one of structure elements I to XI of YZ$_e$—B7, then at least one R of YZ$_e$—B7 is a structure element (C=O)—NH-(A)$_k$-Z.

10. The compound as claimed in claim 9, wherein the heteroatoms are selected from the group consisting of N and O.

11. A method for preparing a compound Q(YZ$_e$)$_b$ according to claim 1, comprising:

A) reacting a compound of structure $QG_b$, in which each G represents a reactive group, which independently of further groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$
with
B) two or more identical or different compounds MZe, wherein M represents a structure element which in each case has one or more of grouping(s) that react with the groups G selected from the group consisting of —NH, —NH$_2$, —OH, —NCO and —COOH,
wherein the following applies:
   R in each case independently of any further R represents a hydrogen atom or an alkyl radical;
   m is an integer selected from the group of integers from 0 through 10,
   each index n is an integer, which independently of any further indices n is selected from the group consisting of 0 and 1,
wherein the compound is a second reaction product from a reaction of the above first reaction product with
C) a further compound according to A) or B), wherein each further compound according to A) or B) has the above meaning, independently of what A) and/or B) represent in the first reaction,
or
the compound is a third reaction product from a reaction of the above second reaction product with
D) a further compound according to A) or B), wherein each further compound according to A) or B) has the above meaning, independently of what A) and/or B) represent in the second reaction.

12. A mixture comprising one, two or a plurality of different compounds as claimed in claim 1.

13. A curable blend, comprising:
(a) one or a plurality of compounds as claimed in claim 1, and
(b) one or a plurality of further components selected from the group consisting of
  (b-1) monomers differing from component (a), which are copolymerizable with component (a),
  (b-2) one or a plurality of fillers,
  (b-3) photoinitiators and initiators for the chemical curing
  (b-4) polymerization inhibitors,
and
  (b-5) solvents.

14. The curable blend as claimed in claim 13, wherein:
said monomers of (b-1) are selected from the group consisting of acrylates and methacrylates, and
said plurality of fillers (b-2) are selected from one or a plurality of nanoscale fillers.

15. A product obtained by curing a composition comprising a compound as claimed in claim 1.

16. A product comprising a compound as claimed in claim 1, wherein said product is a product selected from the group consisting of adhesives, colorings, lacquers, paints or coating compositions, casting compounds, sealants, fillers, laminating resins, molding masses, binding agents or casting resins, electrical or electronic components, magnetic recording materials, micromechanical parts, optical switches, glass fiber coatings, three-dimensional objects by means of stereolithography, printing plates or composites, photographs and holographs.

\* \* \* \* \*

UNITED STATES PATENT AND TRADEMARK OFFICE
CERTIFICATE OF CORRECTION

PATENT NO. : 9,079,828 B2
APPLICATION NO. : 13/248920
DATED : July 14, 2015
INVENTOR(S) : Tobias Blömker et al.

Page 1 of 2

It is certified that error appears in the above-identified patent and that said Letters Patent is hereby corrected as shown below:

In the claims

In Column 83, line 6 of Claim 1, structure elements V. show:

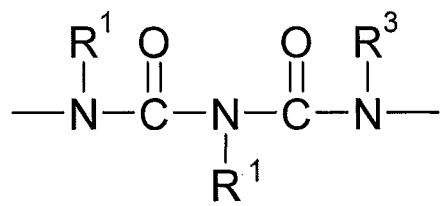

but should show

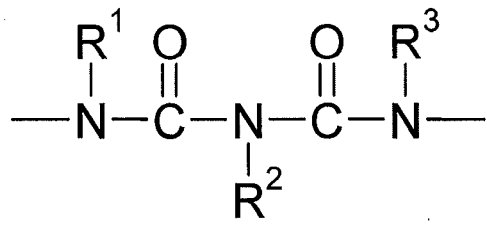

In Column 83, line 31 of Claim 1, structure elements X. show:

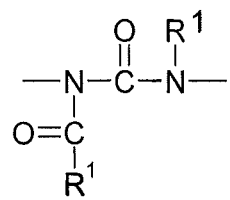

but should show

Signed and Sealed this
First Day of December, 2015

Michelle K. Lee
*Director of the United States Patent and Trademark Office*

CERTIFICATE OF CORRECTION (continued)
U.S. Pat. No. 9,079,828 B2

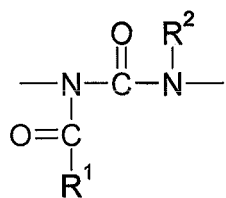

In Column 86, line 11 of Claim 9, structure elements $YZ_e$-B5. show:

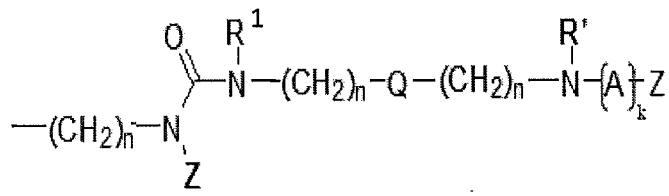

but should show

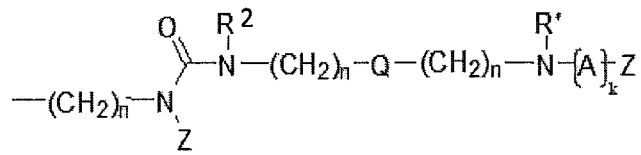

In Column 86, line 52 of Claim 9 reads "$YZ_e$B5, then $R^{2'}$ of $YZ_e$B5 is a structure element"

but should read "$YZ_e$-B5, then $R^{2'}$ of $YZ_e$-B5 is a structure element"

In Column 86, line 61 of Claim 9 reads "$YZ_e$-B7, then at least one R of $YZ_e$-B7 is a structure"

but should read "$YZ_e$-B7, then at least one R' of $YZ_e$-B7 is a structure"

In Column 87, line 27 of Claim 11 reads "or"

but should be deleted